US012582968B2

(12) United States Patent
Devassy et al.

(10) Patent No.: US 12,582,968 B2
(45) Date of Patent: Mar. 24, 2026

(54) DEHYDROGENATION CATALYST

(71) Applicant: SABIC GLOBAL TECHNOLOGIES B.V., Bergen Op Zoom (NL)

(72) Inventors: Biju M. Devassy, Bangalore (IN); Nigit J. Meleppuram, Bangalore (IN); Naresh Dhachapally, Bangalore (IN); Vinod S. Nair, Bangalore (IN)

(73) Assignee: SABIC Global Technologies B.V., Bergen op Zoom (NL)

( * ) Notice: Subject to any disclaimer, the term of this patent is extended or adjusted under 35 U.S.C. 154(b) by 625 days.

(21) Appl. No.: 18/001,145

(22) PCT Filed: Jun. 10, 2021

(86) PCT No.: PCT/IB2021/055121
§ 371 (c)(1),
(2) Date: Dec. 8, 2022

(87) PCT Pub. No.: WO2021/250612
PCT Pub. Date: Dec. 16, 2021

(65) Prior Publication Data
US 2023/0211324 A1      Jul. 6, 2023

(30) Foreign Application Priority Data

Jun. 10, 2020      (EP) .................................... 20179226

(51) Int. Cl.
| | |
|---|---|
| *B01J 23/63* | (2006.01) |
| *B01J 21/04* | (2006.01) |
| *B01J 35/37* | (2024.01) |
| *B01J 37/00* | (2006.01) |
| *B01J 37/02* | (2006.01) |
| *B01J 37/08* | (2006.01) |
| *C07C 5/32* | (2006.01) |

(52) U.S. Cl.
CPC .............. *B01J 23/63* (2013.01); *B01J 21/04* (2013.01); *B01J 35/37* (2024.01); *B01J 37/0009* (2013.01); *B01J 37/0072* (2013.01); *B01J 37/0221* (2013.01); *B01J 37/0236* (2013.01); *B01J 37/088* (2013.01); *C07C 5/325* (2013.01); *C07C 2523/63* (2013.01)

(58) Field of Classification Search
CPC ... B01J 23/63; B01J 21/04; B01J 35/37; B01J 37/0009; B01J 37/0072; B01J 37/0221; B01J 37/0236; B01J 37/088; B01J 2523/00; B01J 37/031; B01J 37/038; B01J 37/04; C07C 5/325; C07C 2523/63
See application file for complete search history.

(56) References Cited

U.S. PATENT DOCUMENTS

| | | | |
|---|---|---|---|
| 2017/0120222 A1 | 5/2017 | Kim et al. | |
| 2019/0126242 A1 * | 5/2019 | Xing ........................ | B01J 23/08 |
| 2020/0129961 A1 | 4/2020 | Fridman et al. | |
| 2020/0223767 A1 * | 7/2020 | Xing ........................ | B01J 23/10 |

FOREIGN PATENT DOCUMENTS

| | | |
|---|---|---|
| WO | WO 2019/011660 | 1/2019 |
| WO | WO 2019/147424 | 8/2019 |

OTHER PUBLICATIONS

International Search Report dated Sep. 15, 2021 for PCT/IB2021/005121.
Written Opinion dated Sep. 15, 2021 for PCT/IB2021/005121.
Im et al., "Physicochemical Stabilization of Pt against Sintering for a Dehydrogenation Catalyst with High Activity, Selectivity, and Durability," ACS Catal. 2016, 6, 2819-2826.

* cited by examiner

*Primary Examiner* — Anthony J Zimmer
*Assistant Examiner* — Abdul-Rahman Yusuf Waleed Smari
(74) *Attorney, Agent, or Firm* — Norton Rose Fulbright US LLP

(57) ABSTRACT

Disclosed are shaped dehydrogenation catalysts, methods for making the catalysts, and methods for dehydrogenating a hydrocarbon using the catalyst. A method for making the shaped dehydrogenation catalyst can include combining a group 13 metal precursor and a group 1 metal precursor with a catalyst support precursor to form a shapeable material, shaping the shapeable material to form a wet shaped material, drying the wet shaped material to form a dry shaped material, and calcining the dry shaped material to form the shaped dehydrogenation catalyst.

20 Claims, 6 Drawing Sheets

DEHYDROGENATION CATALYST

CROSS REFERENCE TO RELATED APPLICATIONS

This application is a national phase under 35 U.S.C. § 371 of International Application No. PCT/IB2021/055121, filed Jun. 10, 2021, which claims the benefit of priority to European Patent Application No. 20179226.4, filed Jun. 10, 2020, the entire contents of each of which are hereby incorporated by reference in their entirety.

FIELD OF INVENTION

The invention generally concerns a shaped dehydrogenation catalyst and a method of making the catalyst. The shaped dehydrogenation catalyst can be made by shaping a shapeable material containing a group 13 metal precursor, a group 1 metal precursor, and a catalyst support precursor.

BACKGROUND OF THE INVENTION

Light alkenes such as ethylene, propylene, butylene, and isobutylene are important raw materials for multiple end products like polymers, rubbers, plastics, octane booster compounds, etc. It is expected that demand for light alkenes will continue to grow. Alkenes can be produced by dehydrogenation of corresponding alkanes. There are many types of catalyst used for dehydrogenation of alkanes. For example, the fixed-bed CATOFIN® process utilizes chromia-alumina catalysts. Disposal of chromium (Cr) catalyst poses problems to the environment and can be costly. Further, long-term exposure to Cr has been associated with cancer in humans.

Alternatives to Cr based catalysts have been attempted. For example, Gallium (Ga) and platinum (Pt) based catalysts have been recognized as promising alkane dehydrogenation materials due to their ability to activate the C—H bond. However, these catalysts show a drop in alkane conversion with reaction and catalyst regeneration cycles. The drop in alkane conversion can be due to loss of Pt dispersion and Pt sintering (see J. Im et. al., *ACS Catal.* 2016, 6, 2819-2826). Gallium (Ga) and platinum (Pt) based catalysts are primarily made by impregnation methods and are costly to produce. As an example, WO2019011660 discloses an alkane dehydrogenation catalysts containing Ga, Pt, Ce, and K on an alumina support. The catalysts are prepared by impregnating an alumina support with a liquid solution containing metal precursors. US 2017/0120222A1 teaches Ga, Ce, Pt and alumina containing catalyst prepared by sol-gel method using aluminium isopropoxide as the alumina source in presence of excess water. During the sol-gel synthesis, for each mole of aluminum isopropoxide, three moles of isopropanol is formed. The excess water and alcohol formed is removed by evaporation. WO2019/147424A1 teaches an alkane dehydrogenation catalyst containing Ga, Ce, Pt, K with a support selected from alumina, silica, zirconia, or titania. The catalyst is prepared by sol-gel method using at least one support precursor selected from an alkoxide in presence excess of water. Such method may generate highly volatile alcohols. The formation of large amount of highly volatile and flammable alcohol along with the use of expensive metal alkoxide as support raw material can lead to serious concerns for large-scale manufacture of the catalyst. There remains a need for additional dehydrogenation catalyst.

SUMMARY OF THE INVENTION

A discovery has been made that provides a solution to at least some of the aforementioned problems associated with catalysts used in the dehydrogenation of hydrocarbons. In one aspect, a solution can include making a Ga, Pt based catalyst using a shaping method rather than using an impregnation method. As illustrated in a non-limiting manner in the Examples section, it was surprisingly found that catalysts made using a shaping method show comparatively higher alkane conversion compared to similar catalysts made by impregnation method.

In one aspect of the present invention, a method of preparing a shaped dehydrogenation catalyst is described. The shaped dehydrogenation catalyst can be used for dehydrogenation of hydrocarbons. The method can include any one of, any combination of, or all of steps (a), (b), (c) and/or (d). In step (a) a group 13 metal precursor, a group 1 metal precursor, and a catalyst support precursor can be combined together to form a shapeable material. In some aspects, and in addition to the group 13 metal precursor and the group 1 metal precursor, a rare earth metal precursor and/or a group 8-11 metal precursor can also be included in step (a). In step (b), the shapeable material can be shaped to form a wet shaped material. In step (c) the wet shaped material can be dried to form a dry shaped material. In step (d) the dry shaped material can be calcined to form the shaped dehydrogenation catalyst. In some aspects, the shapeable material can be in form of a dough. In some aspects, the shaping process can form particles with desired geometric shape. In some aspects, the shaping process can include an extrusion process, a spheronization process or combination thereof. In some aspects, the shaping process can include an extrusion process.

In some aspects, the combining in step (a) can include dissolving the metal precursors in an aqueous solution to form a precursor solution, and adding the precursor solution to the catalyst support precursor to form the shapeable material. In some particular aspects, 0.1 ml to 0.7 ml of the precursor solution can be added per gram of the catalyst support precursor. In some particular aspects, the aqueous solution and/or the precursor solution can include a peptizing agent such as an acidic additive. The pH of the aqueous solution and/or the precursor solution can be below 7.

In some other aspects, the combining in step (a) can include, preparing a solid mixture containing the metal precursors and the catalyst support precursor in solid form, and adding an aqueous solution to the solid mixture to form the shapeable material. In some particular aspects, 0.1 ml to 0.7 ml of the aqueous solution can be added per gram of the solid mixture. In some particular aspects, the aqueous solution can contain a peptizing agent such as an acidic additive. The pH of the aqueous solution can be below 7.

In another aspect, the combining in step (a) can include dissolving at least one metal precursor of step (a) in an aqueous solution to form a precursor solution, preparing a solid mixture containing at least one metal precursor of step (a) and the catalyst support precursor in solid form, and adding the precursor solution to the solid mixture to form the shapeable material. The at least one metal precursor of step (a) dissolved in the aqueous solution may or may not be the same as the at least one metal precursor of step (a) used to prepare the solid mixture. In some particular aspects, 0.1 ml to 0.7 ml of the precursor solution can be added per gram of the solid mixture. In some particular aspects, the aqueous solution and/or the precursor solution can include a peptizing agent such as an acidic additive. The pH of the aqueous solution and/or the precursor solution can be below 7.

In some aspects, the combining in step (a) can include mixing the metal precursors, the catalyst support precursor, a peptizing agent such as an acidic additive(s), and water to form the shapeable material. In some particular aspects, the water can be mixed in an amount 10 wt. % to 70 wt. % of the catalyst support precursor to form the shapeable material. In some aspect, the acidic additive(s) can be mixed in an amount 0.1 wt. % to 30 wt. % or 10 wt. % to 20 wt. % of the catalyst support precursor to form the shapeable material.

In some particular aspects, the acidic additive can contain nitric acid, aluminum nitrate, gallium nitrate, or cerium nitrate or any combination thereof. In some aspects, a metal precursor such as gallium nitrate can be the acidic additive and additional acidic additives such as nitric acid might not be added. In some aspects, the acidic additive can be free of or substantially free of Cr.

In some aspects, the group 13 metal precursor can be a gallium (Ga) precursor. In some particular aspects, the Ga precursor can be a Ga salt and/or a Ga compound. In some aspects, the group 1 metal precursor can be a potassium (K) precursor. In some particular aspects, the K precursor can be a K salt and/or a K compound. In some aspects, the rare earth metal precursor can be a cerium (Ce) precursor. In some particular aspects, the Ce precursor can be a Ce salt and/or a Ce compound. In some aspects, the group 8-11 metal precursor can be a platinum (Pt) precursor. In some particular aspects, the Pt precursor can be a Pt salt and/or a Pt compound. The catalyst support precursor can contain an alumina ($Al_2O_3$) precursor, a zirconia ($ZrO_2$) precursor, a titania ($TiO_2$) precursor, a silica ($SiO_2$) precursor, or any combination thereof. In some aspects, the catalyst support precursor can contain a hydroxide such as aluminum hydroxide, zirconium hydroxide, titanium hydroxide, silicon hydroxide, or any combination thereof. In some aspects, the catalyst support precursor can contain an alumina precursor. In some aspects, the alumina precursor can be aluminum (iii) hydroxide. In some aspects, zirconia precursor can be zirconium (iv) hydroxide. In some aspects, the titania precursor can be titanium (iv) hydroxide. In some aspects, the silica precursor can be silicon (iv) hydroxide. In some aspects, the catalyst support precursor does not contain an aluminum alkoxide such as aluminum isopropoxide. In some particular aspects, the catalyst support precursor can contain aluminum hydroxide. In some aspects, the aluminum hydroxide can be formed by hydration of a transition alumina such as chi alumina or rho alumina. In some aspects, the aluminum hydroxide can be formed by hydration of a transition alumina such as chi alumina or rho alumina during the combining step. In some aspects, the aluminum hydroxide can be gibbsite, bayerite, nordstrandite, boehmite, diaspore, amorphous aluminum hydroxide, or any combination thereof. In some aspects, the drying condition in step (c) can include heating at a temperature 50° C. to 180° C. for 0.1 hours to 25 hours. In some aspects, the calcining condition in step (d) can include heating in presence of air and/or oxygen at a temperature 500° C. to 1000° C., preferably 700° C. to 950° C., for 0.1 hours to 12 hours. In some aspects in step (b) the shapeable material is shaped by an extrusion process, a spheronization process or combination thereof. In some particular aspects in step (b) the shapeable material is shaped by an extrusion process.

In an aspect of the present invention, a shaped dehydrogenation catalyst is described. The shaped dehydrogenation catalyst can be used for dehydrogenation of hydrocarbons.

The shaped dehydrogenation catalyst can contain a group 13 metal oxide, a group 1 metal oxide and a catalyst support. The catalyst support can include alumina, zirconia, titania, or silica, or any combination thereof. In some aspects, the shaped dehydrogenation catalyst can further contain a rare earth metal oxide and a group 8-11 metal oxide. In some aspects, the group 13 metal can be gallium (Ga). In some particular aspects, the shaped dehydrogenation catalyst can contain 1 wt. % to 20 wt. % or 1 wt. % to 10 wt. % of a group 13 metal oxide, e.g. a gallium oxide such as $Ga_2O_3$. In some aspects, the group 1 metal can be potassium (K). In some aspects, the shaped dehydrogenation catalyst can contain 0.1 wt. % to 3 wt. % of a group 1 metal oxide, e.g. a potassium oxide such as $K_2O$. In some aspects, the rare earth metal can be cerium (Ce). In some aspects, the shaped dehydrogenation catalyst can contain 0.1 wt. % to 3 wt. % of a rare earth metal oxide, e.g. a cerium oxide such as $Ce_2O_3$. In some aspects, the group 8-11 metal can be platinum (Pt). In some aspects, the shaped dehydrogenation catalyst can contain 0.001 wt. % to 0.08 wt. % of a group 8-11 metal oxide, e.g. a platinum oxide such as $PtO_2$. In some aspects, the shaped dehydrogenation catalyst can contain 1 wt. % to 20 wt. % of $Ga_2O_3$. In some aspects, the shaped dehydrogenation catalyst can contain 0.1 wt. % to 3 wt. % of $K_2O$. In some aspects, the shaped dehydrogenation catalyst can contain 0.1 wt. % to 3 wt. % of $Ce_2O_3$. In some aspects, the shaped dehydrogenation catalyst can contain 0.001 wt. % to 0.08 wt. % or 0.003 wt. % to 0.08 wt. %, or 0.002 wt. % to 0.012 wt. % of $PtO_2$. In some aspects, the shaped dehydrogenation catalyst comprises: 1 wt. % to 20 wt. % $Ga_2O_3$, 0.1 wt. % to 3 wt. % group 1 metal oxide, 0.001 wt. % to 0.025 wt. % $PtO_2$, and preferably 0.001 wt. % to 0.025 wt. % $PtO_2$, and a catalyst support selected from group consisting of alumina, silica, zirconia, titania, or combination thereof. In some aspects the group 1 metal is potassium (K).

An aspect relates to method for making a shaped dehydrogenation catalyst, wherein the shaped dehydrogenation catalyst comprises: 1 wt. % to 20 wt. % $Ga_2O_3$, 0.1 wt. % to 3 wt. % group 1 metal oxide, 0.002 wt. % to 0.025 wt. % $PtO_2$ and a catalyst support selected from group consisting of alumina, silica, zirconia, titania, or combination thereof, wherein the method comprising: (a) combining a gallium oxide precursor and a group 1 metal precursor with a catalyst support precursor selected from the group consisting of aluminum hydroxide, zirconium hydroxide, titanium hydroxide, silicon hydroxide or any combination thereof, to form a shapeable material; (b) shaping the shapeable material to form a wet shaped material; (c) drying the wet shaped material to form a dry shaped material; and (d) calcining the dry shaped material to form the shaped dehydrogenation catalyst, wherein in step (b) the shapeable material is shaped by an extrusion process, a spheronization process or a combination thereof and/or wherein the dry shaped material is calcined at a temperature 700° C. to 950° C. Preferably, the shaped dehydrogenation catalyst comprises: 1 wt. % to 20 wt. % $Ga_2O_3$, 0.1 wt. % to 3 wt. % group 1 metal oxide, 0.002 wt. % to 0.025 wt. % $PtO_2$ and a catalyst support selected from group consisting of alumina, silica, zirconia, titania, or combination thereof. Preferably the group 1 metal is potassium (K). Preferably in step (a) comprises combining a rare earth metal precursor and a group 8-11 metal precursor along with the group 13 metal precursor and the group 1 metal precursor with the catalyst support precursor to form the shapeable material.

In some aspects, the catalyst support can be alumina. In some particular aspects, the alumina can be gamma-alumina, eta-alumina, delta-alumina, theta-alumina, rho-alumina, chi-alumina, or kappa-alumina, or any combination thereof. In some aspects, the shaped dehydrogenation catalyst can contain Ga, K, Ce, Pt, and a catalyst support containing alumina. In some particular aspects, the shaped dehydrogenation catalyst can contain 1 wt. % to 20 wt. or 1 wt. % to 10 wt. % $Ga_2O_3$, 0.001 wt. % to 0.08 wt. % or 0.003 wt. % to 0.08 wt. % $PtO_2$, 0.1 wt. % to 3 wt. % $Ce_2O_3$, 0.1 wt. % to 3 wt. % $K_2O$, and a catalyst support containing alumina. In other aspects the shaped dehydrogenation catalyst containing 1 wt. % to 20 wt. % $Ga_2O_3$, 0.1 wt. % to 3 wt. % group 1 metal oxide, 0.001 wt. % to 0.025 wt. % $PtO_2$ and a catalyst support selected from group consisting of alumina, silica, zirconia, titania, or combination thereof. The shaped dehydrogenation catalyst can be free of or substantially free of chromium (Cr).

The shaped dehydrogenation catalyst can contain macro-sized particles. In some aspects, the macro-sized particles can have at least one dimension such as length, width, height, diameter equal to or greater than 0.5 mm. The shaped dehydrogenation catalyst e.g. the macro-sized particles of the shaped dehydrogenation catalyst can have a desired geometric shape. The desired geometric shape includes but is not limited to spherical, cube, cuboidal, cylindrical, puck, oval, buckyball, and oblong shapes. Macro-sized particles having other shapes can also be made. In some aspects, the macro-sized particles can have cylindrical shape with a circular, elliptical, ovular, triangular, square, rectangular, pentagonal, or hexagonal cross section, although cylindrical shaped macro-sized particles having a cross-section of other shapes can also be made. In some aspects, the macro-sized particles can have mechanical strength to support its weight and/or withstand the shaping step, drying step, and/or calcination step. In some aspects, the shaped dehydrogenation catalyst e.g. the macro-sized particles of the shaped dehydrogenation catalyst can have an average radial crush strength greater than about 0.5 daN/mm, or preferably greater than about 1 daN/mm, such as 0.5 daN/mm to 3.5 daN/mm, preferably 1 daN/mm to 3.5 daN/mm.

In another aspect, a process for obtaining an unsaturated hydrocarbon by dehydrogenation of a hydrocarbon using the shaped dehydrogenation catalyst is described. The process can include contacting a reactant stream containing a hydrocarbon with a shaped dehydrogenation catalyst of the present invention under conditions suitable to dehydrogenate at least a portion of the hydrocarbon and produce a products stream containing an unsaturated hydrocarbon. In some aspects, the contacting condition can include a temperature 400° C. to 800° C., a pressure 0.1 to 5 bar, or gas hourly space velocity (GHSV) 300 $mlh^{-1}g^{-1}$ to 1000 $mlh^{-1}g^{-1}$ or a combination thereof. In some aspects, the catalyst can be regenerated after performing the dehydrogenation reaction. The regeneration process can include oxidizing used catalyst formed during or after the dehydrogenation reaction. In some aspects, the regeneration process can include contacting the used catalyst with a stream containing air, $O_2$ enriched air, $O_2$, $CO_2$, steam, or any combination thereof at a temperature 500° C. to 900° C. for 0.1 hour to 8 hour. The regenerated catalyst can be re-used in the dehydrogenation reaction. The shaped dehydrogenation catalyst of the present invention can be used over multiple reaction-regeneration cycles without significant drop in alkane conversion and/or alkene selectivity (e.g., less than 15%, less than 10%, less than 5%, less than 3%, less than 1%, or 0% drop in conversion and/or selectivity). In some aspects, the macro-sized particles of the shaped dehydrogenation catalyst can have mechanical strength to withstand the weight of the catalyst bed on top of it and/or to withstand the turbulence of the process streams such as reactant stream, regeneration stream, and/or purge stream.

Another aspect of the invention is a method for making a shaped dehydrogenation catalyst containing 1 wt. % to 20 wt. % $Ga_2O_3$, 0.1 wt. % to 3 wt. % group 1 metal oxide, 0.001 wt. % to 0.025 wt. % $PtO_2$ and a catalyst support selected from group consisting of alumina, silica, zirconia, titania, or combination thereof, wherein the method includes the steps of (a) combining a gallium oxide precursor and a group 1 metal precursor with a catalyst support precursor selected from the group consisting of aluminum hydroxide, zirconium hydroxide, titanium hydroxide, silicon hydroxide or any combination thereof, to form a shapeable material; (b) shaping the shapeable material to form a wet shaped material; (c) drying the wet shaped material to form a dry shaped material; and (d) calcining the dry shaped material to form the shaped dehydrogenation catalyst, wherein in step (b) the shapeable material is shaped by an extrusion process, a spheronization process or a combination thereof and/or wherein the dry shaped material is calcined at a temperature 700° C. to 950° C.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment discussed herein can be implemented with respect to any method or composition of the invention, and vice versa. Furthermore, compositions and systems of the invention can be used to achieve methods of the invention.

The following includes definitions of various terms and phrases used throughout this specification.

The phrase "group 8-11 metal" refers to a metal belonging to group 8, 9, 10 or 11 of the periodic table.

The term "hydrocarbon" refers to i) aliphatic or aromatic and ii) saturated or unsaturated organic compounds. In some aspects, the hydrocarbon can be made of carbon and hydrogen only. The term "unsaturated hydrocarbon" refers to unsaturated aliphatic or aromatic unsaturated organic compounds. In some aspects, the unsaturated hydrocarbon can be made of carbon and hydrogen only.

The terms "about" or "approximately" are defined as being close to as understood by one of ordinary skill in the art. In one non-limiting embodiment, the terms are defined to be within 20%, within 10%, preferably within 5%, more preferably within 1%, and most preferably within 0.5%.

The terms "wt. %," "vol. %," or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%. "Essentially free" includes as having no more than about 0.1% of a component. % can be wt., vol., or mol.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process and systems of the present invention can "comprise," "consist essentially of," or "consist of" particular ingredients, components, compositions, steps, etc. disclosed throughout the specification. With respect to the transitional phrase "consisting essentially of," in one non-limiting aspect, a basic and novel characteristic of the catalysts, compositions, and processes of the present invention are using a shaping method to make the shaped dehydrogenation catalysts. The catalysts can be used in the dehydrogenation reaction of hydrocarbons to produce unsaturated hydrocarbons.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

DETAILED DESCRIPTION OF THE INVENTION

Figures 1A, 1B:
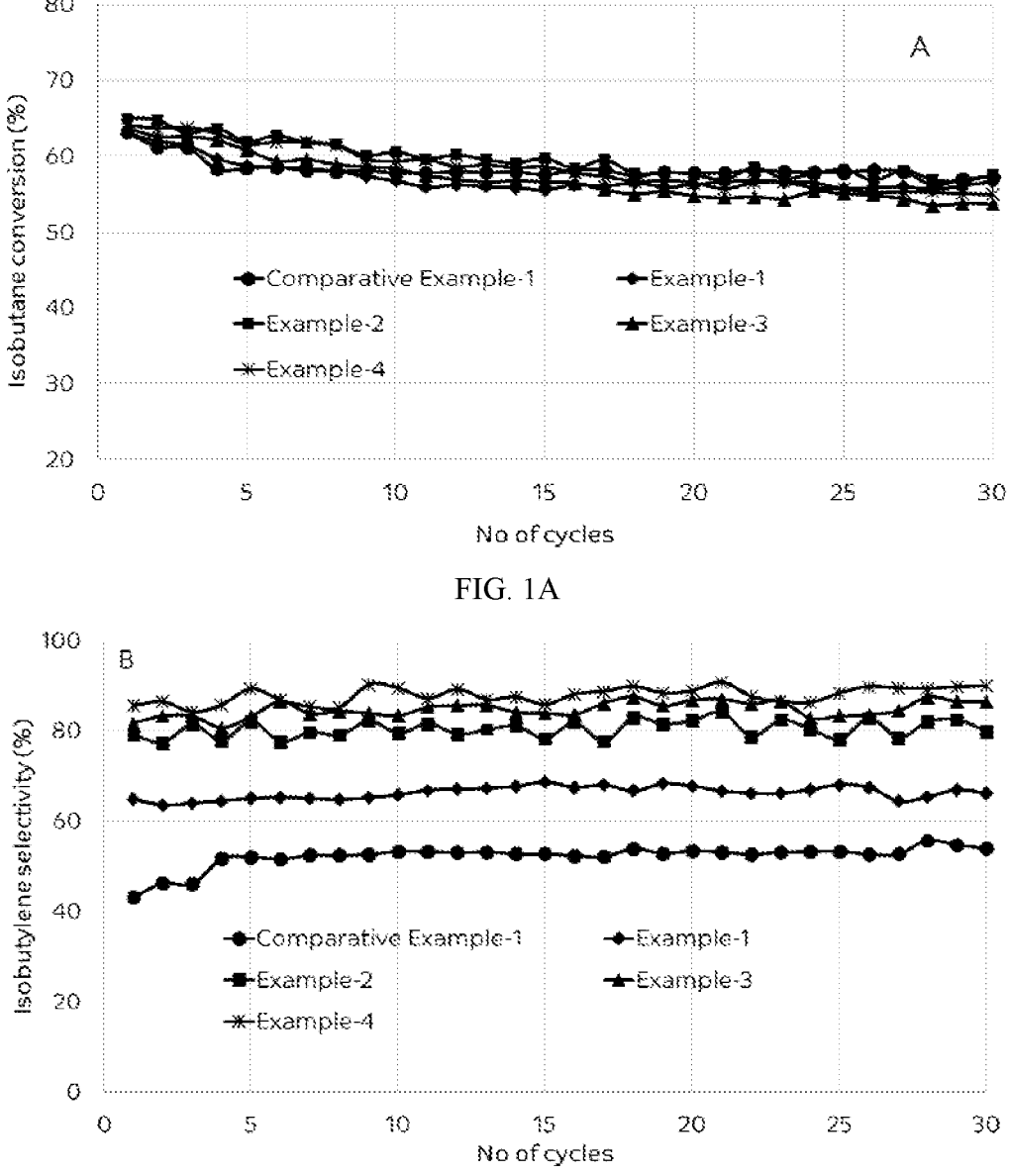
FIGS. 1A-1C: Isobutane conversion (1A), isobutylene selectivity (1B) and isobutylene yield (1C) of catalysts of Examples 1-4 and comparative example 1.

A discovery has been made that provides a solution to at least some of the aforementioned problems associated with catalysts used for dehydrogenation of hydrocarbons. In one aspect, there is disclosed a method for making a shaped dehydrogenation catalyst by a shaping process e.g. extrusion processing rather than by solution/impregnation processing. The produced catalysts exhibit good stability and can be regenerated and used for multiple reaction-regeneration cycles. The shaped dehydrogenation catalysts also exhibit comparatively high conversion rates even after multiple regenerations.

These and other non-limiting aspects of the present invention are discussed in the following sections.

A. Methods of Making a Shaped Dehydrogenation Catalyst

One aspect of the present invention is directed to a method to prepare a shaped dehydrogenation catalyst. The method can include any one of, any combination of, or all of steps (a), (b), (c) and/or (d). In step (a) a group 13 metal precursor, and a group 1 metal precursor can be combined with a catalyst support precursor containing an alumina precursor, a zirconia precursor, a titania precursor, a silica precursor or any combination thereof to form a shapeable material. In some aspects, the catalyst support precursor can be a particulate material. In some aspects, in step (a) a rare earth metal precursor, and a group 8-11 metal precursor along with the group 13 metal precursor, the group 1 metal precursor can be combined with the catalyst support precursor to form the shapeable material. In step (b), the shapeable material can be shaped to form a wet shaped material. In step (c) the wet shaped material can be dried to form a dry shaped material. In step (d) the dry shaped material can be calcined e.g. at 700° C. to 950° C. or 750° C. to 950° C., to form the shaped dehydrogenation catalyst. In some aspects, the group 13 metal can be gallium (Ga) and the group 13 metal precursor can be gallium hydroxide $(Ga(OH)_3)$, gallium nitrate $(Ga(NO_3)_3)$, gallium fluoride $(GaBr_3)$, gallium bromide $(GaBr_3)$, gallium iodide $(GaI_3)$, gallium sulfate $(Ga_2(SO_4)_3)$, gallium oxide $(Ga_2O_3)$, gallium citrate $(GaC_6H_5O_7)$ or gallium acetate $(Ga(C_2H_3O_2)_3)$ or any combination thereof. In some aspects, the group 1 metal can be lithium (Li), sodium (Na), potassium (K), rubidium (Rb), or cesium (Cs), or any combination thereof. In some aspect, the group 1 metal can be K and the group 1 metal precursor can be potassium nitrate $(KNO_3)$, potassium acetate $(KC_2H_3O_2)$, potassium citrate $(K_3C_6H_5O_7)$, potassium oxalate $(C_2K_2O_4)$, potassium carbonate $(K_2CO_3)$, or potassium hydroxide (KOH) or any combination thereof. In some aspects, the rare earth metal can be cerium (Ce) and the rare earth metal precursor can be cerium hydroxide $(Ce(OH)_3)$, cerium oxide $(CeO_2)$ such as colloidal cerium oxide, cerium nitrate $(Ce(NO_3)_3)$, cerium acetate $(CeC_6H_5O_7)$, ammonium ceric nitrate $((NH_4)_2Ce(NO_3)_6)$, ammonium ceric sulfate $((NH_4)_4Ce(SO_4)_4)$, ceric oxide $(CeO_2)$, or ceric chloride $(CeCl_4)$ or any combination thereof. In some aspects, the group 8-11 metal can be ruthenium (Ru), rhodium (Rh), iridium (Ir), palladium (Pd), or platinum (Pt), or any combination thereof. In some aspects, the group 8-11 metal can be Pt and the group 8-11 metal precursor can be tetraamineplatinum nitrate $(Pt(NH_3)_4(NO_3)_2)$, platinum(II) acetate $Pt(C_2H_3O_2)_2$, platinum(II) chloride $(PtCl_2)$, potassium tetracholroplatinate $(K_2PtCl_4)$, ammonium hexachloroplatinate $((NH_4)_2[PtCl_6])$, chloroplatinic acid $(H_2PtCl_6)$, platinum dioxide $(PtO_2)$, or potassium hexachloroplatinate $(K_2PtCl_6)$ or any combination thereof. In some aspects, the alumina precursor can be aluminum hydroxide $(Al(OH)_3)$. In some aspects, the zirconia precursor can be zirconium (iv) hydroxide, zirconium (iv) oxynitrate, zirconium (iv) oxychloride, zirconium (iv) chloride, zirconium (iv) oxide such as colloidal zirconium oxide or any combination thereof. In some aspects, the titania precursor can be titanium (iv) hydroxide, titanium (iv) chloride, titanium (iv) oxide such as colloidal titanium dioxide, or any combination thereof. In some aspects, the silica precursor can be orthosilicic acid ($Si(OH)_4$), alkali metal silicates, colloidal silica, silica gel or any combination thereof. In some aspects, the catalyst support precursor does not include an aluminum alkoxide such as aluminum isopropoxide, a zirconium alkoxide such as zirconium (iv) propoxide, a titanium alkoxide such as titanium (iv) isopropoxide, and/or a silicon alkoxide such as tetraethyl orthosilicate. In some aspects, the catalyst support precursor does not include aluminum, zirconium, titanium and/or silicon compound(s) that liberate(s) organic compound(s) upon hydrolysis. In some aspects, the calcination process in step (d) does not liberate volatile organic compound(s).

In some aspects, combination in step (a) can include dissolving the metal precursors (e.g. i) a group 13 metal precursor, and a group 1 metal precursor, or ii) group 13 metal precursor, a group 1 metal precursor, a rare earth metal precursor and a group 8-11 metal precursor) in an aqueous solution to form a precursor solution and adding the precursor solution to the catalyst support precursor. In some aspects, 0.1 ml to 0.7 ml or at least any one of, equal to any one of, or between any two of 0.1 ml, 0.15 ml, 0.2 ml, 0.25 ml, 0.3 ml, 0.35 ml, 0.4 ml, 0.45 ml, 0.5 ml, 0.55 ml, 0.6 ml, 0.65 ml, and 0.7 ml of the precursor solution can be added per gram of the catalyst support precursor. In some aspects, the aqueous solution and/or the precursor solution can contain a peptizing agent. The peptizing agent is added to get catalyst with required mechanical strength. In some aspects, the peptizing agent can be an acidic additive. In some aspects, the acidic additive can be nitric acid, aluminum nitrate, gallium nitrate, or cerium nitrate or any combinations thereof. In some aspects, the aqueous solution and/or the precursor solution can contain 1 wt. % to 40 wt. % or at least any one of, equal to any one of, or between any two of 1, 2, 3, 4, 5, 6, 7, 8, 9, 10, 11, 12, 13, 14, 15, 16, 17, 18, 19, 20, 22, 24, 26, 28, 30, 32, 34, 36, 38 and 40 wt. % of nitric acid. In some particular aspects, a Ga precursor, a K precursor, a Ce precursor and a Pt precursor can be dissolved in an aqueous solution containing 1 to 40 wt. % of a peptizing agent, e.g., nitric acid to form a precursor solution. In some particular aspects, gallium nitrate $Ga(NO_3)_3$, tetraamineplatinum nitrate ($Pt(NH_3)_4(NO_3)_2$), cerium nitrate $Ce(NO_3)_3$, and potassium nitrate ($KNO_3$) can be dissolved in a aqueous solution containing 1 to 40 wt. % of peptizing agent, e.g., nitric acid to form a precursor solution.

In some aspects, combination in step (a) can include preparing a solid mixture containing the metal precursors (e.g. i) a group 13 metal precursor, and a group 1 metal precursor, or ii) a group 13 metal precursor, a group 1 metal precursor, a rare earth metal precursor and a group 8-11 metal precursor) and the catalyst support precursor and adding an aqueous solution to the solid mixture to form the shapeable material. In some aspects, 0.1 ml to 0.7 ml or at least any one of, equal to any one of, or between any two of 0.1 ml, 0.15 ml, 0.2 ml, 0.25 ml, 0.3 ml, 0.35 ml, 0.4 ml, 0.45 ml, 0.5 ml, 0.55 ml, 0.6 ml, 0.65 ml, and 0.7 ml of the aqueous solution can be added per gram of the solid mixture. In some aspects, the aqueous solution can contain a peptizing agent. In some aspects, the peptizing agent can be an acidic additive. In some aspects, the acidic additive can be nitric acid, nitric acid, aluminum nitrate, gallium nitrate or cerium nitrate or any combination thereof. In some aspects, the aqueous solution can contain 1 wt. % to 40 wt. % or at least any one of, equal to any one of, or between any two of 1, 2, 3, 4, 5, 6, 7, 8, 9, 10, 11, 12, 13, 14, 15, 20, 25, 30, 35, to 40 wt. % of a peptizing agent, e.g., nitric acid.

In some aspects, combination in step (a) can include dissolving at least one metal precursor from step (a) in an aqueous solution to form a precursor solution, preparing a solid mixture containing at least one metal precursor from step (a) and the catalyst support precursor, and adding the precursor solution to the solid mixture to form the shapeable material. In some particular aspects, the group 13 metal precursor, the group 1 metal precursor, and the rare metal precursor can be dissolved in the aqueous solution to form the precursor solution, and the solid mixture can contain the group 8-11 metal precursor and the catalyst support precursor. In some particular aspects, the group 13 metal precursor, the group 1 metal precursor, and the group 8-11 metal precursor can be dissolved in the aqueous solution to form the precursor solution, and the solid mixture can contain the rare earth metal precursor and the catalyst support precursor. In some particular aspects, the group 13 metal precursor, the rare earth metal precursor, and the group 8-11 metal precursor can be dissolved in the aqueous solution to form the precursor solution, and the solid mixture can contain the group 1 metal precursor and the catalyst support precursor. In some particular aspects, the group 1 metal precursor, the rare earth metal precursor, and the group 8-11 metal precursor can be dissolved in the aqueous solution to form the precursor solution, and the solid mixture can contain the group 13 metal precursor and the catalyst support precursor. In some particular aspects, the group 13 metal precursor and the group 1 metal precursor can be dissolved in the aqueous solution to form the precursor solution, and the solid mixture can contain the group 8-11 metal precursor, the rare earth metal precursor and the catalyst support precursor. In some particular aspects, the group 13 metal precursor and the rare earth metal precursor can be dissolved in the aqueous solution to form the precursor solution, and the solid mixture can contain the group 1 metal precursor, the group 8-11 metal precursor and the catalyst support precursor. In some particular aspects, the group 13 metal precursor and the group 8-11 metal precursor can be dissolved in the aqueous solution to form the precursor solution, and the solid mixture can contain the group 1 metal precursor, the rare earth metal precursor and the catalyst support precursor. In some particular aspects, the group 1 metal precursor and the rare earth metal precursor can be dissolved in the aqueous solution to form the precursor solution, and the solid mixture can contain the group 13 metal precursor, the group 8-11 metal precursor and the catalyst support precursor. In some particular aspects, the group 1 metal precursor and the group 8-11 metal precursor can be dissolved in the aqueous solution to form the precursor solution, and the solid mixture can contain the group 13 metal precursor, the rare earth metal precursor and the catalyst support precursor. In some particular aspects, the rare earth metal precursor and the group 8-11 metal precursor can be dissolved in the aqueous solution to form the precursor solution, and the solid mixture can contain the group 13 metal precursor, the group 1 metal precursor and the catalyst support precursor. In some particular aspects, the group 1 metal precursor can be dissolved in the aqueous solution to form the precursor solution, and the solid mixture can contain the group 13 metal precursor, the rare earth metal precursor, the group 8-11 metal precursor and the catalyst support precursor. In some particular aspects, the rare earth metal precursor can be dissolved in the aqueous solution to form the precursor solution, and the solid mixture can contain the group 1 metal precursor, the group 13 metal precursor, the group 8-11 metal precursor and the catalyst support precursor. In some particular aspects, the group 8-11 metal precursor can be dissolved in the aqueous solution to form the precursor solution, and the solid mixture can contain the group 1 metal precursor, the rare earth metal precursor, the group 13 metal precursor and the catalyst support precursor. In some particular aspects, the group 13 metal precursor can be dissolved in the aqueous solution to form the precursor solution, and the solid mixture can contain the group 1 metal precursor, the rare earth metal precursor, the group 8-11 metal precursor and the catalyst support precursor. In some aspects, 0.1 ml to 0.7 ml or at least any one of, equal to any one of, or between any two of 0.1 ml, 0.15 ml, 0.2 ml, 0.25 ml, 0.3 ml, 0.35 ml, 0.4 ml, 0.45 ml, 0.5 ml, 0.55 ml, 0.6 ml, 0.65 ml, and 0.7 ml of the precursor solution can be added per gram of the solid mixture. In some aspects, the aqueous solution and/or the precursor solution can contain a peptizing agent. In some aspects, the peptizing agent can be an acidic additive. In some aspects, the acidic additive can be nitric acid, nitric acid, aluminum nitrate, gallium nitrate, or cerium nitrate or any combination thereof. In some aspects, the acid can be nitric acid. In some aspects, the aqueous solution and/or the precursor solution can contain 1 wt. % to 40 wt. % or at least any one of, equal to any one of, or between any two of 1, 2, 3, 4, 5, 6, 7, 8, 9, 10, 11, 12, 13, 14, 15, 20, 25, 30, 35, to 40 wt. % of peptizing agent e.g. nitric acid.

The shapeable material of the current invention can be sufficiently pliable semisolid mass that can shaped with a shaping process to form a wet shaped material having a desired geometric shape. In some aspects, the shaping process can be an extrusion process, a spheronization process or a combination thereof. In some aspects, the shaping process can be an extrusion process, the shapeable material can be an extrudable material, and the wet shaped materiel can be a wet extrudate. The extrudable material can be pushable and/or drawable through an extrusion die and/or an orifice to form the wet extrudate having a desired cross-sectional shape or configuration. The extrusion of the extrudable material can be performed with any suitable extruder and/or suitable extrusion die and/or orifice, as will be appreciated by those of skill. The die opening and the cross-section of the wet extrudate can have any suitable regular and/or irregular shape. Non-limiting shapes include circular, oval, square, rectangular, pentagonal, hexagonal, rounded square, rounded rectangular, rounded pentagonal, rounded hexagonal, and star shaped. The extrusion die can have one or more opening(s). The extrusion process can be carried out using ram extruder, single screw extruder or twin screw extruder. In some particular aspects, the extrusion die can have circular opening with 0.5, 1, 2, 3, 4, 5, 6, 7, 8, 9 to 10 mm diameter. In some aspects, the extrusion can be performed at room temperature, however extruder barrel temperature can vary. The extruder speed may depend on type of extruder and manufacturer.

In some aspects, drying in step (c) can include heating at a temperature 70° C. to 180° C. or at least any one of, equal to any one of, or between any two of 70° C., 80° C., 90° C., 100° C., 110° C., 120° C., 130° C., 140° C., 150° C., 160° C., 170° C. and 180° C. for 0.1 h to 25 h or at least any one of, equal to any one of, or between any two of 0.1 hour (h), 0.5 h, 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h and 25 h. In some aspects, calcining in step (d) can include heating in presence of air and/or $O_2$ at a temperature of 500° C. to 1000° C. or at least any one of, equal to any one of, or between any two of 500° C., 550° C., 600° C., 650° C., 700° C., 750° C., 800° C., 850° C., 900° C., 950° C. and 1000° C. for 0.5 h to 8 h or at least any one of, equal to any one of, or between any two of 0.5 h, 1 h, 2 h, 3 h, 4 h, 5 h, 6 h, 7 h, and 8 h with. In some aspects, the calcination can include 2 to 20° C. rise in temperature every 1 to 5 minutes. In some aspects, the wet extrudate can be dried at a temperature about 120° C. for about 16 hours in an air oven followed by calcination at about 750° C. for about 2 hours with heating rate about 5° C./min in the presence of air at flow rate about 8 ml $g^{-1}min^{-1}$ to form the shaped dehydrogenation catalyst.

B. Shaped Dehydrogenation Catalyst

The shaped dehydrogenation catalyst can contain a group 13 metal oxide, a group 1 metal oxide and a catalyst support containing alumina, zirconia, titania, silica or any combination thereof. In some aspects, the catalyst can further contain a rare earth metal oxide and a group 8-11 metal oxide. Without intended to be limited by the theory, it is believed that the group 13 metal oxide can function as catalytically active component. The group 1 metal oxide, the rare earth metal oxide, and the group 8-11 metal oxide can each or in combination function as promoters in the catalyst of the current invention. In some particular aspects, the shaped dehydrogenation catalyst can contain 1 wt. % to 20 wt. % or at least any one of, equal to any one of, or between any two of 1 wt. %, 2 wt. %, 3 wt. %, 4 wt. %, 5 wt. %, 6 wt. %, 7 wt. % 8 wt. %, 9 wt. %, 10 wt. %, 12 wt. %, 14 wt. %, 15 wt. %, 16 wt. %, 17 wt. % 18 wt. %, 19 wt. %, and 20 wt. % of the group 13 metal oxide. In some aspects, the group 13 metal oxide can be a gallium (Ga) oxide. In some particular aspects, the Ga oxide can be $Ga_2O_3$. In some aspects, the shaped dehydrogenation catalyst can include other oxides of Ga. In some aspects, the shaped dehydrogenation catalyst can contain 0.1 wt. % to 3 wt. % or at least any one of, equal to any one of, or between any two of 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, and 3 wt. % of the group 1 metal oxide. In some aspects, the group 1 metal can be lithium (Li), sodium (Na), potassium (K), rubidium (Rb), or cesium (Cs). In some particular aspects, the group 1 metal oxide can be a K oxide. In some particular aspects, the K oxide can be $K_2O$. In some aspects, the shaped dehydrogenation catalyst can include other oxides of K. In some aspects, the shaped dehydrogenation catalyst can contain 0.1 wt. % to 3 wt. % or at least any one of, equal to any one of, or between any two of 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, and 3 wt. % of the rare earth metal oxide. In some aspects, the rare earth metal oxide can be a cerium (Ce) oxide. In some particular aspects, the Ce oxide can be $Ce_2O_3$. In some aspects, the shaped dehydrogenation catalyst can include other oxides of Ce. In some aspects, the shaped dehydrogenation catalyst can contain 0.001 wt. % to 0.08 wt. % or 0.003 wt. % to 0.08 wt. % at least any one of, equal to any one of, or between any two of 0.001 wt. %, 0.002 wt. %, 0.005 wt. %, 0.01 wt. %, 0.015 wt. %, 0.02 wt. %, 0.025 wt. %, 0.03 wt. %, 0.035 wt. %, 0.04 wt. %, 0.045 wt. %, 0.05 wt. %, 0.055 wt. %, 0.06 wt. %, 0.065 wt. %, 0.07 wt. %, 0.075 wt. %, and 0.08 wt. %, of the group 8-11 metal oxide. In some aspects, the group 8-11 metal can be ruthenium (Ru), rhodium (Rh), iridium (Ir), palladium (Pd), or platinum (Pt). In some aspects, the group 8-11 metal oxide can be a ruthenium oxide, such as $RuO_2$, a rhodium oxide such as $Rh_2O_3$, an iridium oxide such as $IrO_2$, a palladium oxide such as PdO, or a platinum oxide such as $PtO_2$. In some particular aspects, the group 8-11 metal oxide can be a Pt oxide. In some particular aspects, the Pt oxide can be $PtO_2$. In some aspects, the shaped dehydrogenation catalyst can include other oxides of Pt. In some aspects, the catalyst support can contain alumina. In some particular aspects, the alumina can be gamma-alumina, eta-alumina, delta-alumina, theta-alumina, rho-alumina, chi-alumina, kappa-alumina or any combination thereof.

In some aspects, the shaped dehydrogenation catalyst can have a surface area 50 $m^2$/g to 500 $m^2$/g or at least any one of, equal to any one of, or between any two of 50 $m^2$/g, 75 $m^2$/g, 100 $m^2$/g. 125 $m^2$/g, 150 $m^2$/g, 175 $m^2$/g, 200 $m^2$/g, 210 $m^2$/g, 220 $m^2$/g, 230 $m^2$/g, 240 $m^2$/g. 250 $m^2$/g, 260 $m^2$/g, 270 $m^2$/g, 280 $m^2$/g. 290 $m^2$/g, 300 $m^2$/g, 325 $m^2$/g, 350 $m^2$/g, 375 $m^2$/g, 400 $m^2$/g, 425 $m^2$/g, 450 $m^2$/g, 475 $m^2$/g and 500 $m^2$/g. In some aspects, the macro-sized particles of the shaped dehydrogenation catalyst can have a particle size i.e. diameter 0.5 mm to 5 mm, or at least any one of, equal to any one of, or between any two of 0.5, 1, 2, 3, 4, and 5 mm. In some aspects, the macro-sized particles of the shaped dehydrogenation catalyst can have a length 0.5 mm to 10 mm, or at least any one of, equal to any one of, or between any two of 0.5, 1, 2, 3, 4, 5, 6, 7, 8, 9 and 10 mm and/or a length 2 mm to 15 mm or at least any one of, equal to any one of, or between any two of 2, 3, 4, 5, 6, 7, 8, 9, 10, 11, 12, 13, 14 and 15 mm. In some aspects, the shaped dehydrogenation catalyst e.g. the macro-sized particles of the shaped dehydrogenation catalyst can have an average radial crush strength 0.5 daN/mm to 3.5 daN/mm or at least any one of, equal to any one of, or between any two of 0.5 daN/mm, 1 daN/mm, 1.5 daN/mm, 2 daN/mm, 2.5 daN/mm, 3 daN/mm, and 3.5 daN/mm.

C. Methods of Using a Shaped Dehydrogenation Catalyst

The shaped dehydrogenation catalyst of the current invention can be used for preparing an unsaturated hydrocarbon by dehydrogenation of a hydrocarbon. A reactant stream containing the hydrocarbon can be contacted with the shaped dehydrogenation catalyst, under conditions suitable to dehydrogenate at least a portion of the hydrocarbon and produce a products stream containing the unsaturated hydrocarbon. The contacting conditions can include a temperature 400° C. to 800° C., or at least any one of, equal to any one of, or between any two of 400° C., 425° C., 450° C., 475° C., 500° C., 525° C., 550° C., 575° C., 600° C., 625° C., 650° C., 675° C., 700° C., 725° C., 750° C., 775° C., and 800° C., and/or a pressure 0.2 bar to 5 bar. In some aspects, the catalyst can be regenerated. The regeneration process can include contacting an used catalyst formed during or after the dehydrogenation reaction from the shaped dehydrogenation catalyst, with a stream of air, $O_2$ enriched air, $O_2$, carbon dioxide, or steam or any combination thereof at a temperature 500° C. to 900° C. or at least any one of, equal to any one of, or between any two of 500° C., 525° C., 550° C., 575° C., 600° C., 625° C., 650° C., 675° C., 700° C., 725° C., 750° C., 775° C., 800° C., 825° C., 850° C., 875° C., and 900° C. for 0.05 hour (h) to 8 h or at least any one of, equal to any one of, or between any two of 0.1 h, 0.2 h, 0.3 h, 0.4 h, 0.5 h, 0.6 h, 0.7 h, 0.8 h, 0.9 h, 1 h, 2 h, 3 h, 4 h, 5 h, 6 h, 7 h, and 8 h. The regenerated catalyst can be used for dehydrogenation reaction again. The shaped dehydrogenation catalyst of the current invention can be used over multiple reaction-regeneration cycles without significant or any drop in conversion and selectivity. In some aspects, the regenerated catalyst can be purged with a first gaseous stream between regeneration and reaction steps. In some aspects, the used catalyst can be purged with a second gaseous stream between reaction and regeneration steps. In some particular aspects, the first and/or second gaseous stream can independently include nitrogen ($N_2$), helium (He), steam, or any combination thereof.

In some aspects, the hydrocarbon can be an alkane and the unsaturated hydrocarbon can be an alkene. In some aspects, the hydrocarbon can be an alkyl aromatic compound such as an alkyl benzene and the unsaturated hydrocarbon can be an alkenyl aromatic compound such as a alkenyl benzene. Non-limiting examples of hydrocarbons that can be used in the context of the present invention include ethane, propane, n-butane, iso-butane, or ethyl benzene or any combination thereof. The corresponding unsaturated hydrocarbon can include ethylene, propylene, n-butylene, iso-butylene or styrene or any combination thereof. In some aspects, the hydrocarbon can be ethane and the unsaturated hydrocarbon can be ethylene. In some aspects, the hydrocarbon can be propane and the unsaturated hydrocarbon can be propylene. In some aspects, the hydrocarbon can be n-butane and the unsaturated hydrocarbon can be n-butene. In some aspects, the hydrocarbon can be iso-butane and the unsaturated hydrocarbon can be iso-butene. In some aspects, the hydrocarbon can be ethyl benzene and the unsaturated hydrocarbon can be styrene.

The dehydrogenation process can be performed in a reactor, which can include one or more heating and/or cooling devices (e.g., insulation, electrical heaters, jacketed heat exchangers in the wall) and/or controllers (e.g., computers, flow valves, automated values, inlets, outlets, etc.) that can be used to control the reaction temperature and pressure of the reaction mixture. A single or multiple reactors can be used. The reactors can be positioned parallel and/or in series. In some aspects, the reactors can be a fixed bed reactor, or moving bed reactors. In some particular aspects, the reactor can be a fixed bed reactor. In some aspects, the shaped dehydrogenation catalyst can be used in an existing dehydrogenation plant, which use or used chromia based catalysts for hydrocarbon dehydrogenation. In some aspects, the existing plant can be a CATOFIN® process plant.

EXAMPLES

As part of the disclosure of the present invention, specific examples are included below. The examples are for illustrative purposes only and are not intended to limit the invention. Those of ordinary skill in the art will readily recognize parameters that can be changed or modified to yield essentially the same results.

Comparative Example-1 (Catalyst Preparation)

A comparative catalyst was prepared by co-extrusion method using peptizing agent. Gallium nitrate hydrate (Ga $(NO_3)_3 \cdot xH_2O$), tetraamineplatinum nitrate ($Pt(NH_3)_4$ $(NO_3)_2$) and cerium nitrate hexahydrate ($Ce(NO_3)_3 \cdot 6H_2O$) and boehmite (G-250, Chika Pvt. Ltd., India) materials were used as precursors of gallium, platinum, cerium, and alumina, respectively. Prior to preparing catalyst, metal salts containing dilute nitric acid solution was prepared. To 36 ml of 70 wt % nitric acid, water added and made the solution to 500 ml To prepare metal salts containing nitric acid solution, about 8.253 g of gallium nitrate (anhydrous basis), 5 mL of 1.5% tetraamineplatinum nitrate solution (1.5 g/100 mL solution), and 2.32 g of cerium nitrate hexahydrate, were dissolved in 60 ml of above nitric acid solution and formed clear solution. The formed solution was used as the peptizing agent for the preparation of catalyst. To boehmite powder (94.66 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was then calcined at 750° C. for 2 hours with heating rate 5° C./min in the presence of air (flow rate=8 ml g$^{-1}$min$^{-1}$) in down flow tubular reactor. After calcination, the catalyst was cooled in presence of air and was stored in an airtight container. The obtained extrudate catalyst (size: ~3 mm diameter and ~6-8 mm length) having surface area of 218 m$^2$/g was used for isobutane dehydrogenation reaction.

Comparative Example-2 (Catalyst Preparation)

A comparative catalyst was prepared by co-extrusion method using peptizing agent. Tetraamineplatinum nitrate (Pt(NH$_3$)$_4$(NO$_3$)$_2$), potassium nitrate and cerium nitrate hexahydrate (Ce(NO$_3$)$_3$·6H$_2$O) and boehmite (G-250, Chika Pvt. Ltd., India) materials were used as precursors of platinum, potassium, cerium and alumina, respectively. Prior to preparing catalyst, metal salts containing dilute nitric acid solution was prepared. To 36 ml of 70 wt. % nitric acid, water added and made the solution to 500 ml To prepare metal salts containing nitric acid solution, 5 mL of 1.5% tetraamineplatinum nitrate solution (1.5 g/100 mL solution), 1.466 g of potassium nitrate and 2.32 g of cerium nitrate hexahydrate, were dissolved in 60 ml of above nitric acid solution and formed clear solution. The formed solution was used as the peptizing agent for the preparation of catalyst. To boehmite powder (94.66 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was then calcined at 750° C. for 2 hours with heating rate 5° C./min in the presence of air (flow rate=8 ml g$^{-1}$min$^{-1}$) in down flow tubular reactor. After calcination, the catalyst was cooled in presence of air and was stored in an airtight container. The obtained extrudate catalyst (size: ~3 mm diameter and ~6-8 mm length) having surface area of 210 m$^2$/g was used for isobutane dehydrogenation reaction.

Comparative Example-3 (Catalyst Preparation)

A comparative catalyst was prepared by impregnation method. The alumina extrudates used for the impregnation were prepared using following procedure. The boehmite (G-250, Chika Pvt. Ltd., India) material was extruded using nitric acid as a peptizing agent. To 36 ml of 70 wt % nitric acid, water added and made the solution to 500 ml. To boehmite powder (500 g) was added dropwise above nitric acid solution (370 ml) and the mixture was mixed for about 30 minutes. The obtained dough was then extruded using a lab extruder (Sunsai), using a die with 3.5 mm circular openings. The prepared wet extrudates were dried at 120° C. for 16 hours in air oven. The dried extrudates (160 g) calcined at 750° C. for 4 hours in muffle furnace with heating rate 5° C./min and air flow rate being 480±10 ml/min. The obtained extrudates (size: ~3 mm diameter and ~6-8 mm length) was used for catalyst preparation. The alumina extrudate support (about 100 g) was heat treated in an oven at 120° C. for 16 hours in the presence of air to remove moisture. The dried alumina extrudate support, after cooling to room temperature, was used for catalyst preparation by incipient wetness impregnation method. The catalyst prepared by incipient wetness impregnation of the support with an aqueous solution prepared by dissolving 3.301 g of gallium nitrate (anhydrous basis), 2 mL of 1.5% tetraamineplatinum nitrate solution (1.5 g/100 mL solution), 0.93 g of cerium nitrate hexahydrate, and 0.58 g potassium nitrate in water and made to 14 ml and formed clear solution. The impregnation was carried out by contacting the above prepared impregnation solution with alumina extrudate support (28.58 g) at room temperature. The impregnated alumina support was then kept at room temperature for 12 hours and then dried at 120° C. for 16 hours. The dried sample was then calcined at 750° C. for 2 hours with heating rate 5° C./min in the presence of air (flow rate, 8 ml g$^{-1}$min$^{-1}$) in down flow tubular reactor. After calcination, the catalyst was cooled in presence of air and the catalyst was stored in an air tight container. The obtained catalyst having surface area of 207 m$^2$/g was used for isobutane dehydrogenation reaction.

Example-1 (Catalyst Preparation)

A catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to prepare catalyst, metal salts containing dilute nitric acid solution was prepared. To 36 ml of 70 wt % nitric acid, water added and made the solution to 500 ml. To prepare metal salts containing nitric acid solution, about 8.253 g of gallium nitrate (anhydrous basis), 5 mL of 1.5% tetraamineplatinum nitrate solution (1.5 g/100 mL solution), 2.32 g of cerium nitrate hexahydrate, and 0.484 g potassium nitrate were dissolved in 60 ml of the above nitric acid solution and formed clear solution. The formed solution was used as peptizing agent for the preparation of catalyst. The nitric acid solution containing the metal salts was added dropwise to boehmite powder (94.6 g) and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was then calcined at 750° C. for 2 hours with heating rate 5° C./min in the presence of air (flow rate=8 ml g$^{-1}$min$^{-1}$) in down flow tubular reactor. After calcination, the catalyst was cooled in presence of air and was stored in an airtight container. The obtained extrudate catalyst (size: ~3 mm diameter and ~6-8 mm length) having surface area of 212 m$^2$/g was used for isobutane dehydrogenation reaction.

Example-2 (Catalyst Preparation)

A catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid, water added and made the solution to 500 ml. To prepare metal salts containing nitric acid solution, about 8.253 g of gallium nitrate (anhydrous basis), 5 mL of 1.5% tetraamineplatinum nitrate solution (1.5 g/100 mL solution), 2.32 g of cerium nitrate hexahydrate, and 0.805 g potassium nitrate salts were dissolved in 60 ml of above nitric acid solution and formed clear solution. The formed solution was used as peptizing agent for the preparation of catalyst. To boehmite powder (94.66 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was then calcined at 750° C. for 2 hours with heating rate 5° C./min in the presence of air (flow rate=8 ml g$^{-1}$min$^{-1}$) in down flow tubular reactor. After calcination, the catalyst was cooled in presence of air and was stored in an airtight container. The obtained extrudate catalyst (size: ~3 mm diameter and ~6-8 mm length) having surface area of 210 m$^2$/g was used for isobutane dehydrogenation reaction.

Example-3 (Catalyst Preparation)

A catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid, water added and made the solution to 500 ml. To prepare metal salts containing nitric acid solution, 8.253 g of gallium nitrate (anhydrous basis), 5 mL of 1.5% tetraamineplatinum nitrate solution (1.5 g/100 mL solution), 2.32 g of cerium nitrate hexahydrate, and 1.14 g potassium nitrate salts were dissolved in 60 ml of above nitric acid solution and formed clear solution. The formed solution was used as peptizing agent for the preparation of catalyst. To boehmite powder (94.66 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was then calcined at 750° C. for 2 hours with heating rate 5° C./min in the presence of air (flow rate=8 ml g$^{-1}$min$^{-1}$) in down flow tubular reactor. After calcination, the catalyst was cooled in presence of air and was stored in an airtight container. The obtained extrudate catalyst (size: ~3 mm diameter and ~6-8 mm length) having surface area of 214 m$^2$/g was used for isobutane dehydrogenation reaction

Example-4 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid water added and made the solution to 500 ml. To prepare metal salts containing nitric acid solution, 8.253 g of gallium nitrate (anhydrous basis), 5 mL of 1.5% tetraamineplatinum nitrate solution (1.5 g/100 mL solution), 2.32 g of cerium nitrate hexahydrate, and 1.466 g potassium nitrate salts were dissolved in 60 ml of above nitric acid solution and formed clear solution. The formed solution was used as peptizing agent for the preparation of catalyst. To boehmite powder (94.66 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was then calcined at 750° C. for 2 hours with heating rate 5° C./min in the presence of air (flow rate=8 ml g$^{-1}$min$^{-1}$) in down flow tubular reactor. After calcination, the catalyst was cooled in presence of air and was stored in an airtight container. The obtained extrudate catalyst (size: ~3 mm diameter and ~6-8 mm length) having surface area of 213 m$^2$/g was used for isobutane dehydrogenation reaction.

Example-5 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid water added and made the solution to 500 ml. To prepare metal salts containing nitric acid solution, 8.253 g of gallium nitrate (anhydrous basis), 5 mL of 1.5% tetraamineplatinum nitrate solution (1.5 g/100 mL solution), 2.32 g of cerium nitrate hexahydrate, and 1.466 g potassium nitrate salts were dissolved in 60 ml of above nitric acid solution and formed clear solution. The formed solution was used as peptizing agent for the preparation of catalyst. To boehmite powder (94.66 g) was added dropwise nitric acid solution (60 ml) containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was then calcined at 800° C. for 2 hours with heating rate 5° C./min in the presence of air (flow rate=8 ml g$^{-1}$min$^{-1}$) in down flow tubular reactor. After calcination, the catalyst was cooled in presence of air and was stored in an airtight container. The obtained extrudate catalyst (size: ~3 mm diameter and ~6-8 mm length) having surface area of 213 m$^2$/g was used for isobutane dehydrogenation reaction.

Example-6 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid, water added and made the solution to 500 ml. To prepare metal salts containing nitric acid solution, 8.253 g of gallium nitrate (anhydrous basis), 1 mL of 1.5% tetraamineplatinum nitrate solution (1.5 g/100 mL solution), 2.32 g of cerium nitrate hexahydrate, and 1.466 g potassium nitrate were dissolved in 60 ml of above nitric acid solution and formed clear solution. The formed solution was used as peptizing agent for the preparation of catalyst. To boehmite powder (94.66 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was then calcined at 750° C. for 2 hours with heating rate 5° C./min in the presence of air (flow rate=8 ml g$^{-1}$min$^{-1}$) in down flow tubular reactor. After calcination, the catalyst was cooled in presence of air and was stored in an airtight container. The obtained extrudate catalyst (size: ~3 mm diameter and ~6-8 mm length) having surface area of 213 m$^2$/g was used for isobutane dehydrogenation reaction.

Example-7 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid, water added and made the solution to 500 ml. To prepare metal salts containing nitric acid solution, 8.253 g of gallium nitrate (anhydrous basis), 1 mL of 1.5% tetraamineplatinum nitrate solution (1.5 g/100 mL solution), 2.32 g of cerium nitrate hexahydrate, and 1.466 g potassium nitrate salts were dissolved in 60 ml of above nitric acid solution and formed clear solution. The formed solution was used as peptizing agent for the preparation of catalyst. To boehmite powder (94.66 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 800° C. for 2 hours with heating rate 5° C./min in the presence of air (flow rate=8 ml g-1min-1) in down flow tubular reactor. The obtained extrudate catalyst size: ~3 mm diameter and ~6-8 mm length.

Example-8 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid water added and made the solution to 500 ml. To prepare metal salts containing nitric acid solution, 8.253 g of gallium nitrate (anhydrous basis), 1 mL of 1.5% tetraamineplatinum nitrate solution (1.5 g/100 mL solution), 2.32 g of cerium nitrate hexahydrate, and 1.466 g potassium nitrate salts were dissolved in 60 ml of above nitric acid and formed clear solution. The formed solution was used as peptizing agent for the preparation of catalyst. To boehmite powder (94.66 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 850° C. for 2 hours with heating rate 5° C./min in the presence of air (flow rate=8 ml g-1min-1) in down flow tubular reactor. The obtained extrudate catalyst size: ~3 mm diameter and ~6-8 mm length.

Example-9 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid water added and made the solution to 500 ml. To prepare metal salts containing nitric acid solution, 8.253 g of gallium nitrate (anhydrous basis), 1.2 mL of 0.25% tetraamineplatinum nitrate solution (0.25 g/100 mL solution), 2.32 g of cerium nitrate hexahydrate, and 1.466 g potassium nitrate were dissolved in 60 ml of above nitric acid solution and formed clear solution. The formed solution was used as peptizing agent for the preparation of catalyst. To boehmite powder (94.66 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 800° C. for 2 hours with heating rate 5° C./min in the presence of air (flow rate=8 ml g-1min-1) in down flow tubular reactor. The obtained extrudate catalyst size: ~3 mm diameter and ~6-8 mm length.

Example-10 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and bayerite ((Pural-BT, SASOL) materials were used as precursors of gallium, platinum, cerium, potassium and alumina, respectively. Prior to preparing catalyst, metal salts containing dilute nitric acid solution was prepared. To 287 ml of 70 wt % nitric acid, water added and made the solution to 500 ml. To prepare metal salts containing nitric acid solution, 7.15 g of gallium nitrate (anhydrous basis), 4.3 mL of 1.5% tetraamineplatinum nitrate solution (1.5 g/100 mL solution), 2.01 g of cerium nitrate hexahydrate, and 0.421 g potassium nitrate were dissolved in 20 ml of above nitric acid solution and formed clear solution. The formed solution was used as peptizing agent for the preparation of catalyst. To Bayerite powder (95.7 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 750° C. for 2 hours with heating rate 5° C./min in the presence of air (flow rate=8 ml g-1min-1) in down flow tubular reactor. The obtained extrudate catalyst size: ~3 mm diameter and ~6-8 mm length.

Example-11 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid, water added and made the solution to 500 ml. To prepare metal salts containing nitric acid solution, 20.466 g of gallium nitrate (anhydrous basis), 3.3 mL of 1.5% tetraamineplatinum nitrate solution (1.5 g/100 mL solution), 1.546 g of cerium nitrate hexahydrate, and 0.977 g potassium nitrate were dissolved in 33 ml of above nitric acid solution and formed clear solution. The formed solution was used as peptizing agent for the preparation of catalyst. To boehmite powder (55.06 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 800° C. for 2 hours with heating rate 5° C./min in the presence of air (flow rate=8 ml g-1min-1) in down flow tubular reactor. The obtained extrudate catalyst size: ~3 mm diameter and ~6-8 mm length.

Example-12 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid water added and made the solution to 500 ml. To prepare metal salts containing nitric acid solution, 8.186 g of gallium nitrate (anhydrous basis), 0.67 mL of 1.5% tetraamineplatinum nitrate solution (1.5 g/100 mL solution), 1.546 g of cerium nitrate hexahydrate, and 0.966 g potassium nitrate were dissolved in 35 ml of above nitric acid solution and formed clear solution. The formed solution was used as peptizing agent for the preparation of catalyst. To boehmite powder (61.28 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 800° C. for 2 hours with heating rate 5° C./min in the presence of air (flow rate=8 ml g-1min-1) in down flow tubular reactor. The obtained extrudate catalyst size: ~3 mm diameter and ~6-8 mm length.

Example-13 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to preparing catalyst, metal salts containing dilute nitric acid solution was prepared. To 36 ml of 70 wt % nitric acid water added and made the solution to 500 ml. To prepare metal salts containing nitric acid solution, 10.915 g of gallium nitrate (anhydrous basis), 0.67 mL of 1.5% tetraamineplatinum nitrate solution (1.5 g/100 mL solution), 1.546 g of cerium nitrate hexahydrate, and 0.966 g potassium nitrate were dissolved in 35 ml of above nitric acid solution and formed clear solution. The formed solution was used as peptizing agent for the preparation of catalyst. To boehmite powder (59.9 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 800° C. for 2 hours with heating rate 5° C./min in the presence of air (flow rate=8 ml g-1min-1) in down flow tubular reactor. The obtained extrudate catalyst size: ~3 mm diameter and ~6-8 mm length.

Example-14 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and boehmite (G-250, Chika Pvt. Ltd., India) materials were used as precursors of gallium, platinum, cerium, potassium and alumina, respectively. Prior to prepare catalyst, aqueous solution containing metal salts were prepared. To prepare metal salts containing aqueous solution, 13.644 g of gallium nitrate (anhydrous basis), 0.67 mL of 1.5% tetraamineplatinum nitrate solution (1.5 g/100 mL solution), 1.546 g of cerium nitrate hexahydrate, and 1.288 g potassium nitrate were dissolved in 35 ml of water and formed clear solution. The formed solution was used as peptizing agent for the preparation of catalyst. To boehmite powder (59.1 g) was added dropwise above aqueous metal salts solution and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 800° C. for 2 hours with heating rate 5° C./min in the presence of air (flow rate=8 ml g-1min-1) in down flow tubular reactor. The obtained extrudate catalyst size: ~3 mm diameter and ~6-8 mm length. The final calculated composition of catalysts of comparative examples are provided in Table 1 and final catalyst composition of catalysts of examples are provided in Table 2.

Example-15 (Catalyst Preparation)

The catalyst was prepared by co-extrusion method using peptizing agent. Gallium nitrate hydrate (Ga(NO$_3$)$_3$·xH$_2$O), tetraamineplatinum nitrate (Pt(NH$_3$)$_4$(NO$_3$)$_2$), cerium nitrate hexahydrate (Ce(NO$_3$)$_3$·6H$_2$O), potassium nitrate (KNO$_3$) and pseudoboehmite alumina (Chika Pvt. Ltd. India) materials were used as precursors of gallium, platinum, cerium, potassium and alumina, respectively. Prior to preparing catalyst, metal salts containing dilute nitric acid solution was prepared. To 14.4 ml of 70 wt. % nitric acid, water added and made the solution to 500 ml. To prepare 100 g of final catalyst, 10.92 g of gallium nitrate (anhydrous basis), 1.32 mL of 1.5% tetraamineplatinum nitrate solution (1.5 g/100 mL solution), 3.07 g of cerium nitrate hexahydrate, and 1.94 g potassium nitrate salts were dissolved in 2% nitric acid solution and formed clear solution. Finally made metal ions containing 234 ml of nitric acid solution. The formed solution was used as peptizing agent for the preparation of catalyst. To boehmite powder (130.3 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 800° C. for 2 hours with heating rate 5° C./min in the presence of air (flow rate=8 ml $g^{-1}min^{-1}$) in down flow tubular reactor. The obtained extrudate catalyst size: ~3 mm diameter and ~6-8 mm length.

Example-16 (Catalyst Preparation)

The catalyst was prepared by co-extrusion method using peptizing agent. Gallium nitrate hydrate ($Ga(NO_3)_3 \cdot xH_2O$), tetraamineplatinum nitrate ($Pt(NH_3)_4(NO_3)_2$), cerium nitrate hexahydrate ($Ce(NO_3)_3 \cdot 6H_2O$), potassium nitrate ($KNO_3$) and pseudoboehmite alumina (Chika Pvt. Ltd. India) materials were used as precursors of gallium, platinum, cerium, potassium and alumina, respectively. Prior to preparing catalyst, metal salts containing dilute nitric acid solution was prepared. To 14.4 ml of 70 wt % nitric acid, water added and made the solution to 500 ml. To prepare 100 g of final catalyst, 10.92 g of gallium nitrate (anhydrous basis), 0.66 mL of 1.5% tetraamineplatinum nitrate solution (1.5 g/100 mL solution), 3.07 g of cerium nitrate hexahydrate, and 1.94 g potassium nitrate salts were dissolved in 2% nitric acid solution and formed clear solution. Finally made metal ions containing 234 ml of nitric acid solution. The formed solution was used as peptizing agent for the preparation of catalyst. To boehmite powder (130.3 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 800° C. for 2 hours with heating rate 5° C./min in the presence of air (flow rate=8 ml $g^{-1}min^{-1}$) in down flow tubular reactor. The obtained extrudate catalyst size: ~3 mm diameter and ~6-8 mm length.

Example-17 (Catalyst Preparation)

The catalyst was prepared by co-extrusion method using peptizing agent. Gallium nitrate hydrate ($Ga(NO_3)_3 \cdot xH_2O$), tetraamineplatinum nitrate ($Pt(NH_3)_4(NO_3)_2$), cerium nitrate hexahydrate ($Ce(NO_3)_3 \cdot 6H_2O$), potassium nitrate ($KNO_3$) and pseudoboehmite alumina (Chika Pvt. Ltd. India) materials were used as precursors of gallium, platinum, cerium, potassium and alumina, respectively. Prior to preparing catalyst, metal salts containing dilute nitric acid solution was prepared. To 14.4 ml of 70 wt % nitric acid, water added and made the solution to 500 ml. To prepare 100 g of final catalyst, 10.92 g of gallium nitrate (anhydrous basis), 0.66 mL of 1.5% tetraamineplatinum nitrate solution (1.5 g/100 mL solution), 3.07 g of cerium nitrate hexahydrate, and 1.94 g potassium nitrate salts were dissolved in 2% nitric acid solution and formed clear solution. Finally made metal ions containing 234 ml of nitric acid solution. The formed solution was used as peptizing agent for the preparation of catalyst. To boehmite powder (130.3 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 850° C. for 2 hours with heating rate 5° C./min in the presence of air (flow rate=8 ml $g^{-1}min^{-1}$) in down flow tubular reactor. The obtained extrudate catalyst size: ~3 mm diameter and ~6-8 mm length.

Example-18 (Catalyst Preparation)

The catalyst was prepared by co-extrusion method using peptizing agent. Gallium nitrate hydrate ($Ga(NO_3)_3 \cdot xH_2O$), tetraamineplatinum nitrate ($Pt(NH_3)_4(NO_3)_2$), cerium nitrate hexahydrate ($Ce(NO_3)_3 \cdot 6H_2O$), potassium nitrate ($KNO_3$) and pseudoboehmite alumina (Chika Pvt. Ltd. India) materials were used as precursors of gallium, platinum, cerium, potassium and alumina, respectively. Prior to preparing catalyst, metal salts containing dilute nitric acid solution was prepared. To 14.4 ml of 70 wt % nitric acid, water added and made the solution to 500 ml. To prepare 100 g of final catalyst, 10.92 g of gallium nitrate (anhydrous basis), 0.66 mL of 1.5% tetraamineplatinum nitrate solution (1.5 g/100 mL solution), 3.07 g of cerium nitrate hexahydrate, and 1.94 g potassium nitrate salts were dissolved in 2% nitric acid solution and formed clear solution. Finally made metal ions containing 234 ml of nitric acid solution. The formed solution was used as peptizing agent for the preparation of catalyst. To boehmite powder (130.3 g) was added dropwise nitric acid solution containing metal salts and the mixture was mixed for about 30 minutes. The obtained dough was then extruded using a lab extruder (Sunsai), using a die having circular openings with 3.5 mm diameter. The prepared wet extrudates were dried at 120° C. for 16 hours in air oven. The dried sample was calcined at 900° C. for 2 hours with heating rate 5° C./min in the presence of air (flow rate=8 ml g-1min-1) in down flow tubular reactor. The obtained extrudate catalyst size: ~3 mm diameter and ~6-8 mm length.

The final calculated composition of catalysts of comparative examples are provided in Table 1 and final catalyst composition of catalysts of examples are provided in Table 2.

TABLE 1

| Catalyst composition of comparative examples | | | | | |
|---|---|---|---|---|---|
| Comparative Example | $Al_2O_3$ (wt %) | $Ga_2O_3$ (wt %) | $Ce_2O_3$ (wt %) | $K_2O$ (wt %) | Pt (ppmwt) | Calcination Temp. (° C.) |
| 1 | 94.7 | 4 | 1.2 | 0 | 505 | 750 |
| 2 | 97.8 | 0 | 1.2 | 0.9 | 521 | 750 |
| 3 | 93.9 | 4 | 1.2 | 0.9 | 497 | 750 |

TABLE 2

| | | Catalyst composition of examples | | | | |
| Example | $Al_2O_3$ (wt %) | $Ga_2O_3$ (wt %) | $Ce_2O_3$ (wt %) | $K_2O$ (wt %) | Pt (ppmw) | Calcination Temp. (° C.) |
| --- | --- | --- | --- | --- | --- | --- |
| 1 | 94.5 | 4.0 | 1.2 | 0.3 | 503 | 750 |
| 2 | 94.3 | 4.0 | 1.2 | 0.5 | 502 | 750 |
| 3 | 94.1 | 4.0 | 1.2 | 0.7 | 501 | 750 |
| 4 | 93.9 | 4.0 | 1.2 | 0.9 | 500 | 750 |
| 5 | 93.9 | 4.0 | 1.2 | 0.9 | 500 | 800 |
| 6 | 93.9 | 4.0 | 1.2 | 0.9 | 100 | 750 |
| 7 | 93.9 | 4.0 | 1.2 | 0.9 | 100 | 800 |
| 8 | 93.9 | 4.0 | 1.2 | 0.9 | 100 | 850 |
| 9 | 93.9 | 4.0 | 1.2 | 0.9 | 20 | 800 |
| 10 | 94.5 | 4.0 | 1.2 | 0.3 | 498 | 750 |
| 11 | 82.8 | 15.0 | 1.2 | 0.9 | 505 | 800 |
| 12 | 91.9 | 6.0 | 1.2 | 0.9 | 101 | 800 |
| 13 | 89.9 | 8.0 | 1.2 | 0.9 | 101 | 800 |
| 14 | 87.7 | 9.9 | 1.2 | 1.2 | 100 | 800 |
| 15 | 93.9 | 4.0 | 1.2 | 0.9 | 100 | 800 |
| 16 | 93.9 | 4.0 | 1.2 | 0.9 | 50 | 800 |
| 17 | 93.9 | 4.0 | 1.2 | 0.9 | 50 | 850 |
| 18 | 94.5 | 4.0 | 1.2 | 0.3 | 50 | 900 |

Example-19 (Catalyst Crush Strength Measurements)

A sample of ~40 g of catalyst extradites were dried for 3 hours in an oven at 400° C. After cooling the catalyst in a desiccator, 30 extrudates were used for the measurement of radial crush strength. Individual extrudate measured in length, placed between two flat surfaces, and subjected to a compressive force. The force required to break the extrudate is measured. The force applied at the moment of break is determined in decanewton (daN) and the results are expressed in daN/mm. The results of selected examples are provided in Table 3.

TABLE 3

| | Radial Crush Strength | |
| Example | Average Radial Crush strength (dN/mm) | STDEV |
| --- | --- | --- |
| 4 | 2.12 | 0.82 |
| 7 | 2.21 | 0.99 |
| 12 | 1.83 | 1.12 |
| 13 | 1.7 | 1.24 |
| 14 | 2.3 | 1.4 |

Example-20 (Catalyst Performance)

The prepared catalysts were tested for dehydrogenation of isobutane to isobutylene. The dehydrogenation reaction was carried out in a tubular fixed-bed quartz reactor. The details of catalyst loading and reactor were as follows: catalyst weight=4.0 g, catalyst particle size=0.4-0.5 mm, reactor ID=16 mm, reactor OD=19 mm. Isobutane (99.9 vol. %) was used as the feed. Quartz chips with size of 1 to 1.4 mm were loaded above the catalyst bed. Nitrogen purge separated between dehydrogenation and regeneration/oxidation steps. The total feed flow in the dehydrogenation step is corresponds to GHSV=600 $mLh^{-1}g^{-1}$. The reactor outlet gases were analyzed by online gas chromatograph (Agilent 6890, Agilent Scientific Instruments, USA) equipped with a flame ionization detector for hydrocarbon analysis and thermal conductivity detector for hydrogen analysis. The reactant and products flow rates were measured using Ritter type wet gas flow meter. The reactor was operated at atmospheric pressure and in a cyclic mode with the following steps:

1. Oxidation in air at 650° C. for 20 min;
2. Purge with nitrogen at 650° C. for 5 min;
3. Cooling with nitrogen from 650° C. to 585° C. and hold for 20 min at 585° C. for temperature stabilization;
4. Start isobutane feed flow for dehydrogenation at 585° C. for 21 min; and
5. GC analysis at $20^{th}$ minute from the start of the isobutane feed
6. Steps 1-5 were repeated for 30 cycles.

For Examples 15 to 18, the catalysts were tested for dehydrogenation of isobutane to produce isobutylene, and the reactor was operated at 0.5 bar partial pressure of isobutane and in a cyclic mode with the following steps:

1. Oxidation in air at 650° C. for 10 min;
2. Purge with nitrogen at 650° C. for 5 min;
3. Cooling with nitrogen from 650° C. to 575° C. and hold for 20 min at 575° C. for temperature stabilization;
4. Start isobutane and nitrogen mixture (1:1 volume) feed flow for dehydrogenation at 575° C. for 10 min;
5. GC analysis at $09^{th}$ minute from the start of the isobutane feed; and
6. Steps 1-5 were repeated for 125 cycles.

Figure 1C:
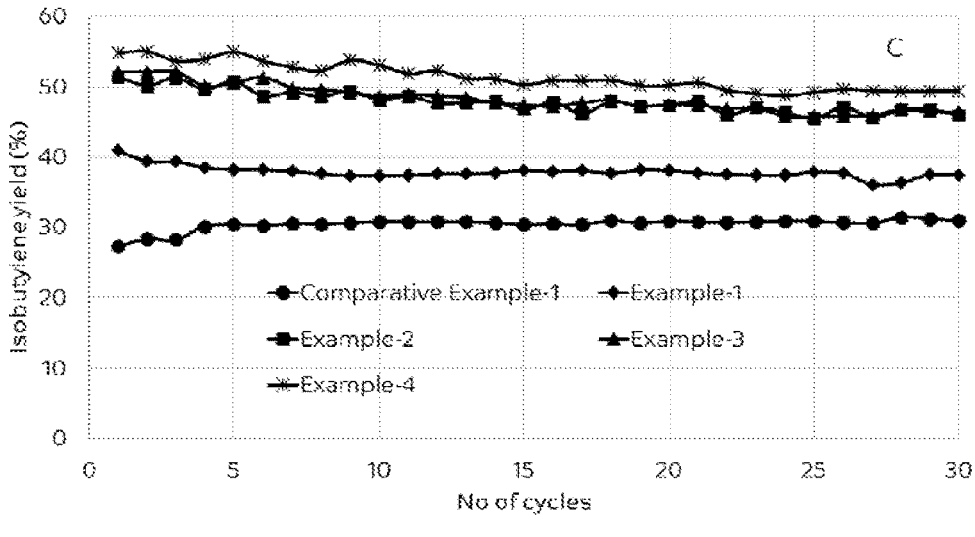

The performance of catalysts (Comparative Example-1 and Example-1 to 4) are shown in FIG. 1A (conversion), FIG. 1B (selectivity) and FIG. 1C (yield). Comparison of isobutane conversion, isobutylene selectivity and isobutylene yield are given in Table 4. The results clearly show that isobutane conversion decreased marginally from ~60% to ~56% as the $K_2O$ content in the catalyst increased from 0% to 0.9%. On the other hand, the selectivity to isobutylene is increased significantly from ~59.5% to ~90% and isobutylene yield increased from ~35.8% to ~50% with increasing $K_2O$ content from 0% to 0.9%.

Figure 2A:
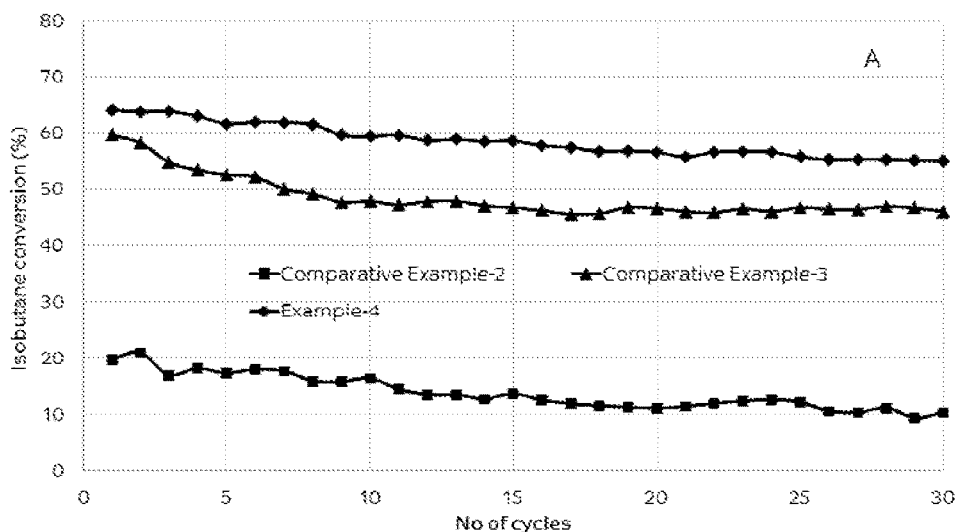
FIGS. 2A-2C: Isobutane conversion (2A), isobutylene selectivity (2B) and isobutylene yield (2C) of catalysts of Example 4 and comparative examples 2-3.
Figure 2B:
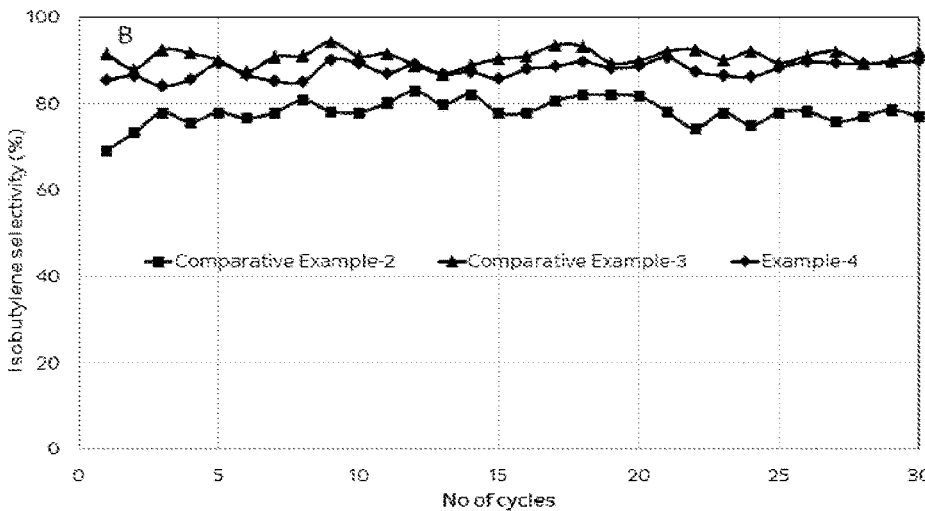
Figure 2C:
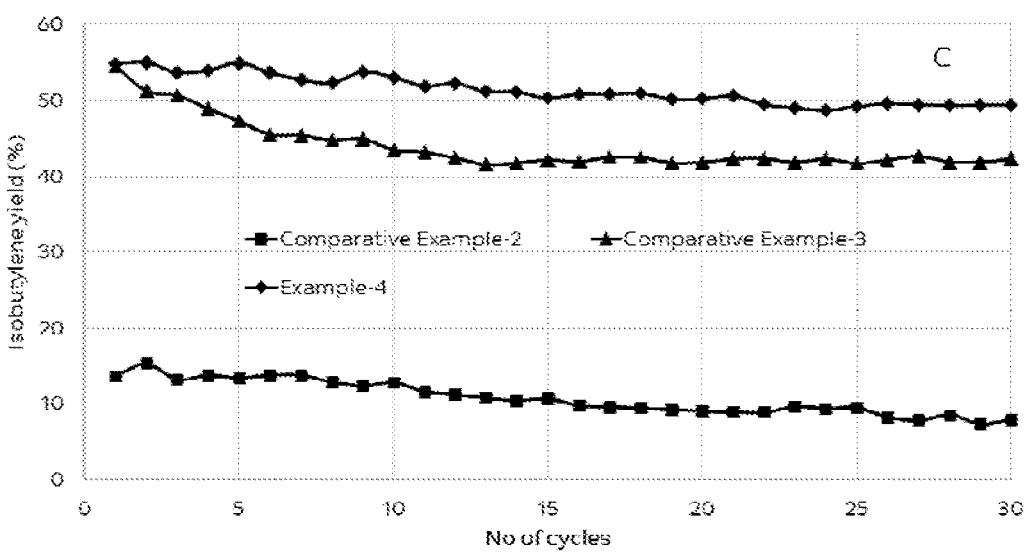

The performance of Comparative Example-2 (without $Ga_2O_3$), Comparative Example-3 (catalyst preparation by impregnation method), and Example 4 is shown in FIG. 2A (conversion), FIG. 2B (selectivity) and FIG. 2C (yield). Isobutane conversion, isobutylene selectivity and isobutylene yield are also given in Table 4. The catalyst of Comparative Example-2 show that isobutane conversion and isobutylene selectivity is ~11% and ~78%, respectively. The results indicate that Gallium oxide is the main active component for dehydrogenation reaction. The performance of catalyst (Comparative Example-3) prepared by impregnation method shows that isobutane conversion decreased to ~46% without effecting isobutylene selectivity. Catalysts of example 4 shows better isobutane conversion (%) than the catalysts of comparative example 2 and of 3.

Catalysts synthesized by the inventive method showed better performance compared to the catalyst prepared by impregnation method. The results clearly indicate that the method of preparation of catalyst is very important to get the better performance. Another important outcome from the above experiment is that gallium oxide is a main an active component for isobutane dehydrogenation.

TABLE 4

Isobutane conversion, isobutylene selectivity and isobutylene yield for catalysts from
Comparative Examples 1-3 and Examples 1-11 (Average data from 15-30 cycles)

| | Before aging | | | After aging | | |
|---|---|---|---|---|---|---|
| Example | Isobutane conversion (%) | Isobutylene selectivity (%) | Isobutylene yield (%) | Isobutane conversion (%) | Isobutylene selectivity (%) | Isobutylene yield (%) |
| Comparative Example-1 | 60.2 | 59.5 | 35.8 | — | — | — |
| Comparative Example-2 | 11.3 | 78.3 | 8.9 | — | — | — |
| Comparative Example-3 | 46.3 | 91.1 | 42.2 | — | — | — |
| Example-1 | 59.1 | 73.9 | 43.8 | — | — | — |
| Example-2 | 57.8 | 81.0 | 46.8 | — | — | — |
| Example-3 | 56.0 | 87.0 | 48.7 | — | — | — |
| Example-4 | 55.7 | 90.0 | 50.1 | 47.9 | 90.5 | 43.3 |
| Example-5 | 51.6 | 89.8 | 46.4 | — | — | — |
| Example-6 | 56.1 | 92.9 | 52.1 | 50.7 | 94.6 | 47.9 |
| Example-7 | 54.9 | 92.3 | 50.7 | 52.9 | 95.2 | 50.3 |
| Example-8 | 54.9 | 94.1 | 51.7 | 52.3 | 95.1 | 49.7 |
| Example-9 | 52.2 | 93.7 | 48.9 | 54.2 | 94.4 | 51.2 |
| Example-10 | 57.7 | 57.8 | 33.3 | — | — | — |
| Example-11 | 45.6 | 79.2 | 36.1 | — | — | — |

Example 21 (Accelerated Aging Protocol)

After initial performance evaluation, stability of the catalyst of Example-4 was evaluated using an accelerated aging protocol. The details of the aging protocol are given below. After completing initial (30 cycles) performance as per procedure described in Example-16, aging of the catalyst of Example-4 was carried out at 700° C. for 3 days. The other experimental details are as follows: catalyst weight=4.0 g, GHSV for all gases=600 mL $g^{-1}h^{-1}$, except for air=1200 mL $g^{-1}$ $h^{-1}$.

1. Oxidation in air at 700° C. for 20 min;
2. Purge with nitrogen at 700° C. for 5 min;
3. Isobutane feed flow at 700° C. for 5 min;
4. Purge with nitrogen at 700° C. for 5 min;
5. Steps 1-4 were repeated for 75 cycles (3 days).

Figure 3A:
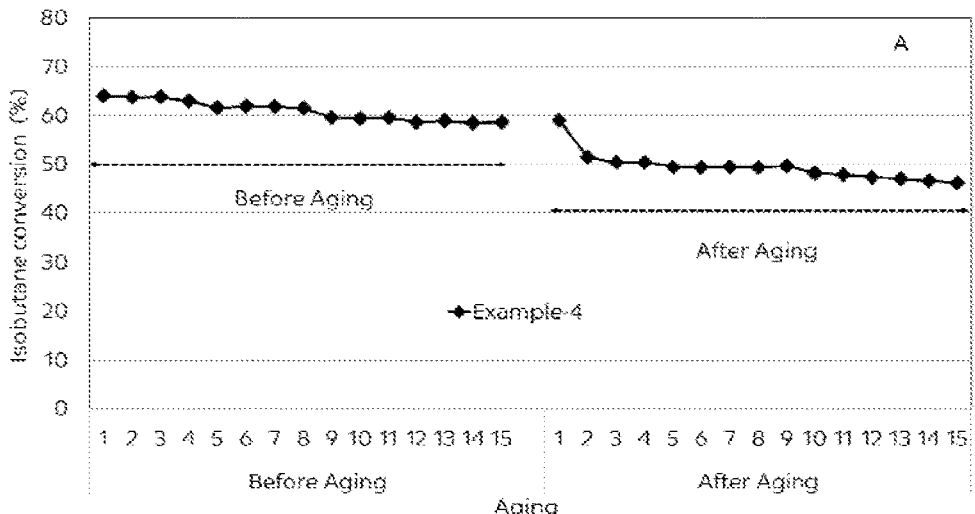
FIGS. 3A-3C: Isobutane conversion (3A), isobutylene selectivity (3B) and isobutylene yield (3C) of catalysts of Example 4 before and after aging at 700° C.
Figure 3B:
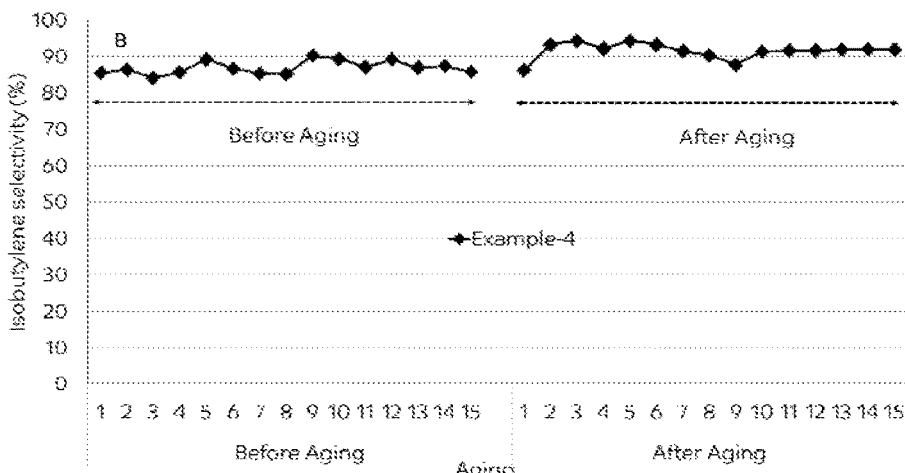
Figure 3C:
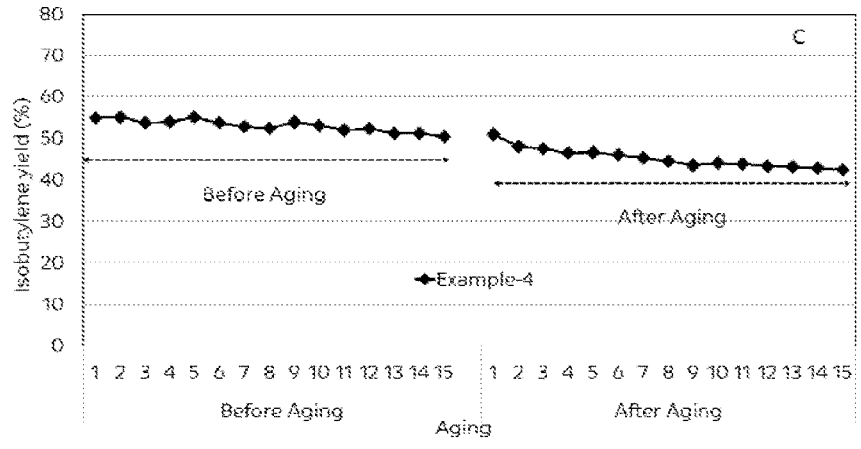

Catalyst (Example-4) performance before and after aging at 700° C. is shown in FIG. 3A (conversion), FIG. 3B (selectivity) and FIG. 3C (yield). The results clearly show that before aging average isobutane conversion for 1 to 15 cycles are ~61% and decreased to 57.5% after aging. Average isobutylene selectivity before aging is ~87% and increased to 93% after aging with no change in isobutylene yield before and after aging.

Example-22 (Accelerated Aging Protocol)

After initial performance evaluation, stability of the catalyst of example-4, example-6, example-7, example-8 and example-9 was evaluated using an accelerated aging protocol. The details of the aging protocol are given below. After complete initial (30 cycles) performance as per procedure described in example-16, aging of the catalysts (Example-4, Example-6, Example-7, Example-8 and Example-9) was carried out at 820° C. for 3 days. The other details are as follows: catalyst weight=4.0 g, GHSV for air=1200 mL $g^{-1}$ $h^{-1}$, GHSV for $N_2$=1500 mL $g^{-1}$ $h^{-1}$ and GHSV for Isobutane=400 mL $g^{-1}$ $h^{-1}$.

1. Oxidation in air at 820° C. for 15 min;
2. Purge with nitrogen at 820° C. for 3 min;
3. Isobutane feed flow at 820° C. for 3 min;
4. Purge with nitrogen at 820° C. for 3 min;
5. Steps 1-4 were repeated for 135 cycles (3 days).

Figure 4A:
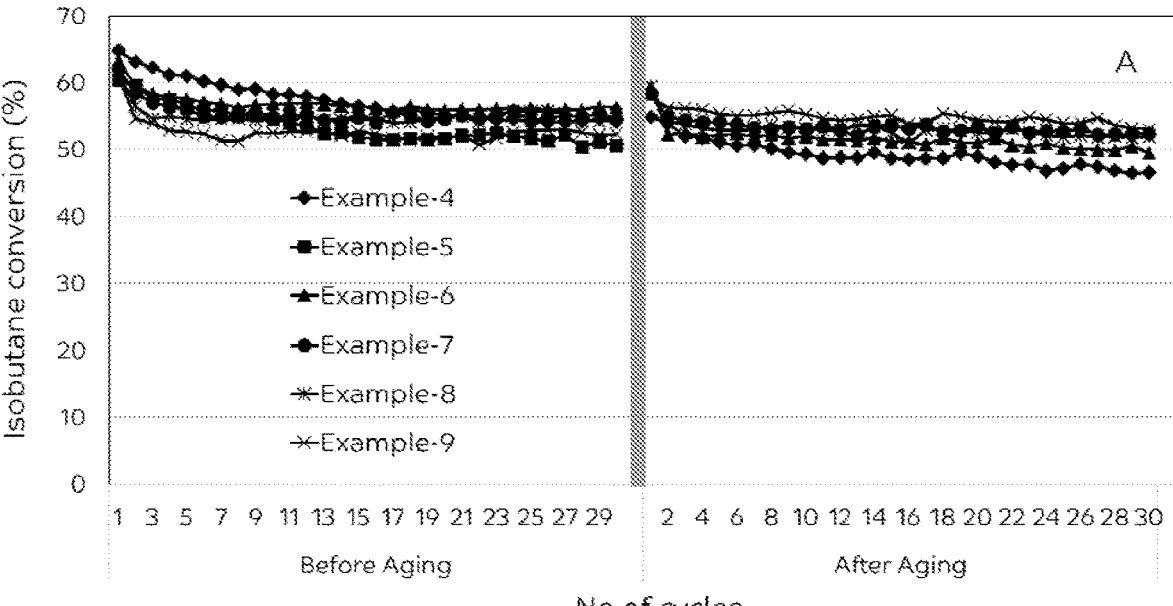
FIGS. 4A-4C: Isobutane conversion (4A), isobutylene selectivity (4B) and isobutylene yield (4C) of catalysts of Examples 4-9 before aging and Examples 4, 6-9 after aging at 820° C.
Figure 4B:
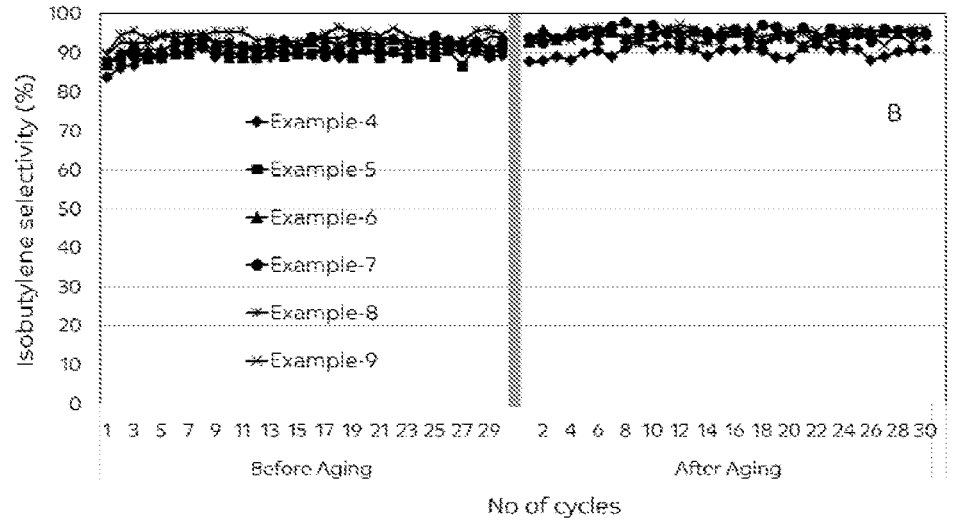
Figure 4C:
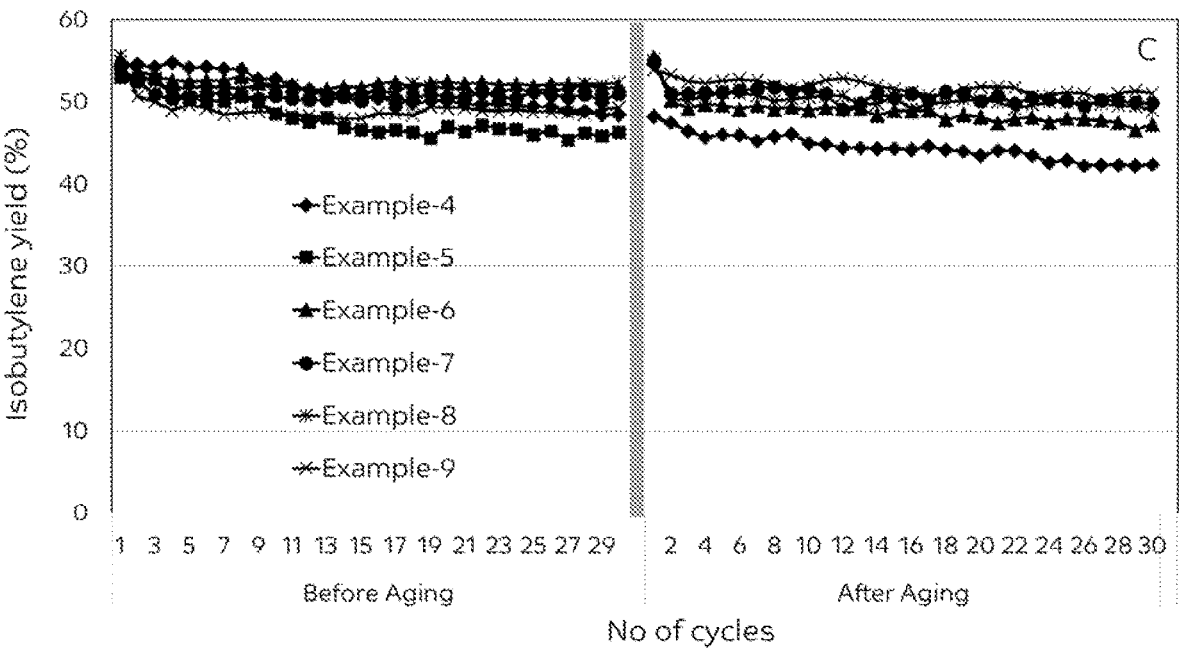

Catalysts performance before aging (Example-4-9) and after aging (Example-4, Example-6, Example-7, Example-8 and Example-9) at 820° C. is shown in FIG. 4A (conversion), FIG. 4B (selectivity) and FIG. 4C (yield). The average isobutane conversion decreased with cycles for catalyst prepared with 500 ppm Pt and calcined at 800° C. (Example-5) in comparison with catalyst containing 500 ppm Pt calcined at 750° C. (Example-4).

Average isobutane conversion is similar for catalyst prepared with an amount of Pt 500 ppm (Example-4) and 100 ppm (Example-6), where catalysts were calcined at 750° C.; however, average isobutane conversion after aging is higher for catalyst having 100 ppm Pt, which clearly indicates that catalyst with lower platinum is beneficial to attain catalyst with higher stability.

Average isobutane conversion and isobutylene yield is similar for catalysts containing 100 ppm Pt calcined at 750° C. (Example-6), 800° C. (Example-7) and 850° C. (Example-8). However after aging average isobutane conversion and isobutylene yield is higher for catalyst containing 100 ppm Pt calcined at 800° C. and 850° C. in comparison with catalyst containing 100 ppm Pt calcine at 750° C. which clearly indicates that catalyst with lower platinum content calcined at higher temperature make the catalyst more stable.

Average isobutane conversion and isobutylene yield is less for catalyst having 20 ppm Pt calcined at 800° C. (Example-9) in comparison with catalyst containing 100 ppm Pt calcined at 800° C. (Example-7). After aging, catalyst containing 20 ppm Pt calcined at 800° C. shown higher isobutane conversion and isobutylene yield in comparison with catalyst containing 100 ppm Pt, which further indicate that catalyst with lower platinum content with appropriate high temperature calcination is a methodology to design catalyst with high stability.

Figure 5A:
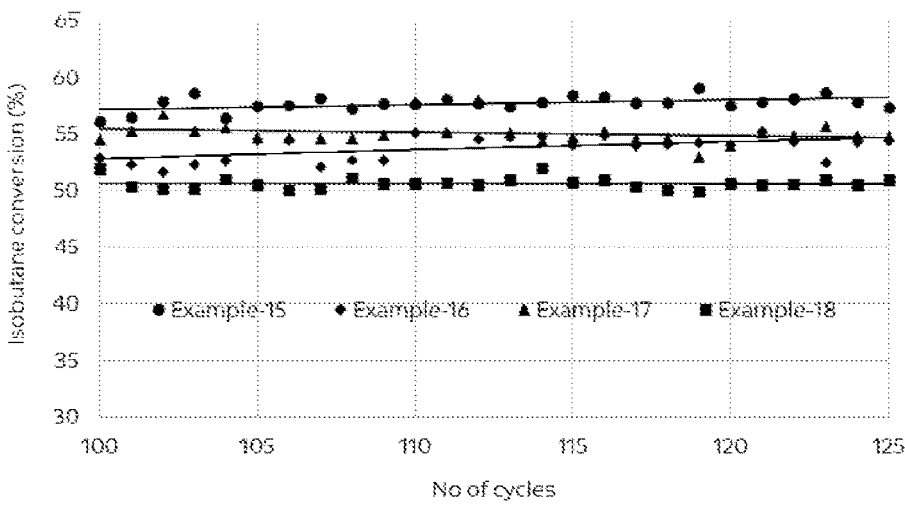
FIGS. 5A-5C: Isobutane conversion (5A), isobutylene selectivity (5B), and isobutylene yield (5C) of catalysts of Examples 15 to 18.
Figure 5B:
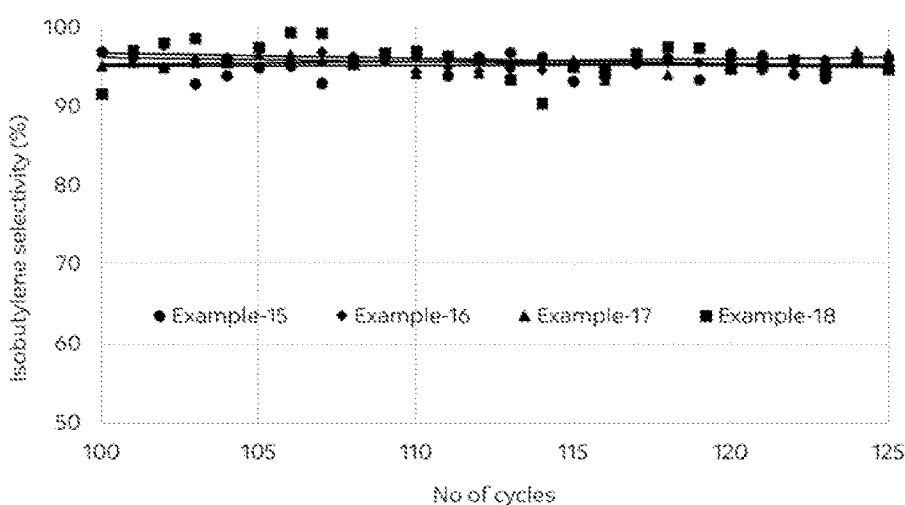
Figure 5C:
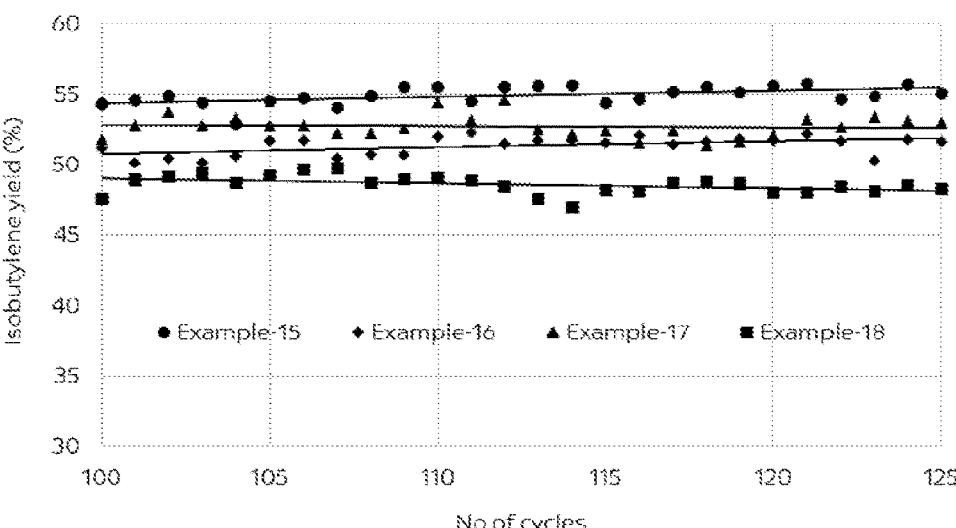

Average isobutane conversion, isobutylene selectivity and isobutylene yield (FIGS. 5A-5C) for catalysts having 50 ppm Pt calcined at 800° C. (Example-16), 850° C. (Example-17) and 900° C. (Example-18) were shown in Table 5. The results indicate that catalyst with 50 ppm Pt calcined at 850° C. is more active for isobutane conversion in comparison with the catalyst having 50 ppm Pt calcined at 800° C. and 900° C. The isobutylene yield of catalyst with 50 ppm Pt calcined at 850° C. is closer to that of catalyst with 100 ppm Pt calcined at 800° C.

TABLE 5

Isobutane conversion, isobutylene selectivity
and isobutylene yield for catalysts from Examples-15
to 18 (Average data from 101-125 cycles)

| Example | Isobutane conversion (%) | Isobutylene selectivity (%) | Isobutylene yield (%) |
|---|---|---|---|
| Example-15 | 57.8 | 95.1 | 55 |
| Example-16 | 53.8 | 95.5 | 51.3 |
| Example-17 | 55.1 | 95.7 | 52.8 |
| Example-18 | 50.6 | 96.1 | 48.6 |

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for making a shaped dehydrogenation catalyst, the method comprising:
(a) combining a group 13 metal precursor and a group 1 metal precursor with a catalyst support precursor, to form a shapeable material;
(b) shaping the shapeable material to form a wet shaped material;
(c) drying the wet shaped material to form a dry shaped material; and
(d) calcining the dry shaped material to form the shaped dehydrogenation catalyst; wherein the shaped dehydrogenation catalyst comprises particles with an average radial crush strength greater than 0.5 daN/mm.

2. The method of claim 1, wherein step (a) comprises combining a rare earth metal precursor and a group 8-11 metal precursor along with the group 13 metal precursor and the group 1 metal precursor with the catalyst support precursor to form the shapeable material.

3. The method of claim 1, wherein the combining in step (a) comprises:
dissolving the metal precursors in an aqueous solution to form a precursor solution; and
adding the precursor solution to the catalyst support precursor to form the shapeable material.

4. The method of claim 3, wherein the aqueous solution comprises an acidic additive.

5. The method of claim 1, wherein the combining in step (a) comprises:
preparing a solid mixture comprising the metal precursors and the catalyst support precursor; and

adding an aqueous solution comprising an acidic additive to the solid mixture to form the shapeable material.

6. The method of claim 1, wherein the combining in step (a) comprises:
dissolving at least one metal precursor of step (a) in an aqueous solution to form a precursor solution;
preparing a solid mixture comprising at least one metal precursor of step (a) and the catalyst support precursor; and
adding the precursor solution to the solid mixture to form the shapeable material.

7. The method of claim 6, wherein the aqueous solution comprises an acidic additive.

8. The method of claim 1, wherein the group 13 metal is gallium (Ga) and/or the group 1 metal is potassium (K).

9. The method of claim 2, wherein the rare earth metal is cerium (Ce) and/or wherein the group 8-11 metal is platinum (Pt).

10. The method of claim 1, wherein the catalyst support precursor comprises, aluminum hydroxide, zirconium hydroxide, titanium hydroxide, silicon hydroxide, or any combination thereof.

11. The method of claim 10, wherein the aluminum hydroxide is gibbsite, bayerite, nordstrandite, boehmite, diaspore, amorphous aluminum hydroxide, or any combination thereof.

12. The method of claim 1, wherein the shaped dehydrogenation catalyst comprises Ga, K, Ce, Pt and a catalyst support comprising alumina, silica, zirconia, titania, or any combination thereof, and/or wherein the shaped dehydrogenation catalyst comprises a gallium oxide, a potassium oxide, a cerium oxide, a platinum oxide and a catalyst support comprising alumina, zirconia, titania, or any combination thereof.

13. The method of claim 1, wherein the shaped dehydrogenation catalyst comprises 1 wt. % to 20 wt. % $Ga_2O_3$, 0.1 wt. % to 3 wt. % $K_2O$, 0.1 wt. % to 3 wt. % $Ce_2O_3$, 0.002 wt. % to 0.012 wt. % $PtO_2$ and a catalyst support comprising alumina and/or wherein at least one dimension selected from length, width, height, and diameter is equal to or greater than 0.5 mm.

14. The method of claim 1, wherein in step (b) the shapeable material is shaped by an extrusion process, a spheronization process or a combination thereof and/or wherein the dry shaped material is calcined at a temperature from 700° C. to 950° C.

15. The method of claim 4, wherein the acidic additive comprises nitric acid, aluminum nitrate, gallium nitrate, cerium nitrate, or any combination thereof.

16. A method for making a shaped dehydrogenation catalyst, wherein the shaped dehydrogenation catalyst comprises:
1 wt. % to 20 wt. % $Ga_2O_3$, 0.1 wt. % to 3 wt. % group 1 metal oxide, 0.002 wt. % to 0.025 wt. % $PtO_2$ and a catalyst support selected from the group consisting of alumina, silica, zirconia, titania, or any combination thereof,
the method comprising:
(a) combining a gallium oxide precursor and a group 1 metal precursor with a catalyst support precursor selected from the group consisting of aluminum hydroxide, zirconium hydroxide, titanium hydroxide, silicon hydroxide, or any combination thereof, to form a shapeable material;
(b) shaping the shapeable material to form a wet shaped material;

(c) drying the wet shaped material to form a dry shaped material; and (d) calcining the dry shaped material to form the shaped dehydrogenation catalyst, wherein in step (b) the shapeable material is shaped by an extrusion process, a spheronization process, or a combination thereof, and wherein the shaped dehydrogenation catalyst comprises particles with an average radial crush strength greater than 0.5 daN/mm, and/or wherein the dry shaped material is calcined at a temperature from 700° C. to 950° C.

17. The method of claim 1, wherein the shaped dehydrogenation catalyst comprises: 1 wt. % to 20 wt. % $Ga_2O_3$, 0.1 wt. % to 3 wt. % group 1 metal oxide, 0.002 wt. % to 0.025 wt. % $PtO_2$ and a catalyst support selected from the group consisting of alumina, silica, zirconia, titania, or any combination thereof.

18. The method of claim 1, wherein the group 1 metal is potassium (K).

19. The method of claim 17, wherein step (a) comprises combining a rare earth metal precursor and a group 8-11 metal precursor along with the group 13 metal precursor and the group 1 metal precursor with the catalyst support precursor to form the shapeable material.

20. The method of claim 18, wherein step (a) comprises combining a rare earth metal precursor and a group 8-11 metal precursor along with the group 13 metal precursor and the group 1 metal precursor with the catalyst support precursor to form the shapeable material.

* * * * *